US012558412B2

(12) United States Patent (10) Patent No.: US 12,558,412 B2
Del Giudice et al. (45) Date of Patent: Feb. 24, 2026

(54) VACCINATION OF IMMUNOCOMPROMISED SUBJECTS

(71) Applicant: Seqirus UK Limited, Berkshire (GB)

(72) Inventors: Giuseppe Del Giudice, Berkshire (GB); Rino Rappuoli, Berkshire (GB); Steven Black, Berkshire (GB); Uwe Nicolay, Berkshire (GB)

(73) Assignee: Seqirus UK Limited, Berkshire (GB)

( * ) Notice: Subject to any disclaimer, the term of this patent is extended or adjusted under 35 U.S.C. 154(b) by 0 days.

(21) Appl. No.: 19/182,766

(22) Filed: Apr. 18, 2025

(65) Prior Publication Data

US 2025/0242011 A1 Jul. 31, 2025

Related U.S. Application Data

(63) Continuation of application No. 18/935,840, filed on Nov. 4, 2024, now abandoned, which is a continuation of application No. 18/746,583, filed on Jun. 18, 2024, now abandoned, which is a continuation of application No. 18/394,260, filed on Dec. 22, 2023, now abandoned, which is a continuation of application No. 18/232,504, filed on Aug. 10, 2023, now abandoned, which is a continuation of application No. 18/188,587, filed on Mar. 23, 2023, now abandoned, which is a continuation of application No. 18/053,496, filed on Nov. 8, 2022, now abandoned, which is a continuation of application No. 17/854,942, filed on Jun. 30, 2022, now abandoned, which is a continuation of application No. 16/901,185, filed on Jun. 15, 2020, now Pat. No. 11,406,701, which is a continuation of application No. 16/739,358, filed on Jan. 10, 2020, now Pat. No. 10,716,844, which is a continuation of application No. 15/514,154, filed as application No. PCT/IB2015/057388 on Sep. 25, 2015, now abandoned.

(60) Provisional application No. 62/149,351, filed on Apr. 17, 2015, provisional application No. 62/056,019, filed on Sep. 26, 2014.

(30) Foreign Application Priority Data

Nov. 6, 2014 (EP) .................................... 14192174

(51) Int. Cl.
| | |
|---|---|
| *A61P 31/16* | (2006.01) |
| *A61K 39/12* | (2006.01) |
| *A61K 39/145* | (2006.01) |
| *A61K 39/295* | (2006.01) |
| *A61K 39/39* | (2006.01) |
| *A61P 37/04* | (2006.01) |
| *C12N 7/00* | (2006.01) |
| *A61K 39/00* | (2006.01) |

(52) U.S. Cl.
CPC ............ *A61K 39/145* (2013.01); *A61K 39/12* (2013.01); *A61K 39/39* (2013.01); *C12N 7/00* (2013.01); *A61K 2039/545* (2013.01); *A61K 2039/55566* (2013.01); *C12N 2760/16134* (2013.01); *C12N 2760/16234* (2013.01)

(58) Field of Classification Search
CPC ........ A61K 2039/545; A61K 2039/523; A61K 2039/5258; A61K 2039/70; A61K 39/145
See application file for complete search history.

(56) References Cited

U.S. PATENT DOCUMENTS 11,406,701 B2 8/2022 Del Giudice et al.

FOREIGN PATENT DOCUMENTS

| | | | |
|---|---|---|---|
| AU | 2007/327367 A1 | 6/2008 | |
| JP | 2014-040396 A | 3/2014 | |
| WO | WO 2002/058737 A1 | 8/2002 | |
| WO | WO 2003/101397 A1 | 12/2003 | |
| WO | WO 2003/103571 A1 | 12/2003 | |
| WO | WO 2006/100109 A1 | 9/2006 | |
| WO | WO 2007/021672 A2 | 2/2007 | |
| WO | WO 2007/129290 A1 | 11/2007 | |
| WO | WO 2010/003670 A1 | 1/2010 | |
| WO | WO 2010/092479 A2 | 8/2010 | |
| WO | WO 2011/095402 A1 | 8/2011 | |
| WO | WO 2012/149301 A2 | 11/2012 | |
| WO | WO 2014/083194 A1 | 6/2014 | |
| WO | WO 2014/095944 A1 | 6/2014 | |

OTHER PUBLICATIONS

Lim et al. "Recent advances, approaches and challenges in the development of universal influenza vaccines", Influenza and Other Respiratory Viruses, 2024, 18:e13276:1-13.*
Agrippal® 2012 Label.
Ambrose et al. "The rationale for quadrivalent influenza vaccines," *Human Vaccines & Immunotherapeutics* 2012, 8(1), pp. 81-88. https://www.tandfonline.com/doi/10.4161/hv.8.1.17623?url_ver=Z39.88-2003&rfr_id=ori:rid:crossref.org&rfr_dat=cr_pub%20%200pubmed.
Annual general meeting 2022—May 3, 2022 [PowerPoint Slides]. Sanofi. https://www.sanofi.com/assets/dotcom/content-app/events/annual-general-meeting/2022/2022-sanofi-agm-2022-en-final-2.pdf.

(Continued)

*Primary Examiner* — Barry A Chestnut

(74) *Attorney, Agent, or Firm* — Finnegan, Henderson, Farabow, Garrett & Dunner, LLP

(57) ABSTRACT

Disclosed herein are methods for enhancing immune responses to a vaccine in immunocompromised individuals, including those receiving a statin therapy. Related products are also provided.

20 Claims, No Drawings

(56)         References Cited

OTHER PUBLICATIONS

Appendices—Research & Development - Apr. 27, 2018 [PowerPoint Slides]. Sanofi. https://www.sanofi.com/assets/dotcom/content-app/events/quaterly-results/2018/q1-2018-en/Q1_2018_Appendices_FINAL.pdf.

Aspinall, R. et al., "Challenges for vaccination in the elderly," *Immunity and Ageing* 2007, 4(9), 9 pages. https://link.springer.com/article/10.1186/1742-4933-4-9.

Baxter, D. "Evaluating the case for trivalent or quadrivalent influenza vaccines," *Human Vaccines & Immunotherapeutics* 2016, 12(10), pp. 2712-2717. https://www.tandfonline.com/doi/full/10.1080/21645515.2015.1091130.

Beck et al., "Influenza Vaccination for Immunocompromised Patients: Systematic Review and Meta-analysis by Etiology," *The Journal of Infectious Diseases* 2012, 206(8), pp. 1250-1259. https://academic.oup.com/jid/article-abstract/206/8/1250/856364.

Becker DL et al. "High-dose inactivated influenza vaccine is associated with cost savings and better outcomes compared to standard dose inactivated influenza vaccine in Canadian seniors," *Human Vaccines & Immunotherapeutics* 2016, 12(12), pp. 3036-3042. https://www.tandfonline.com/doi/10.1080/21645515.2016.1215395#abstract.

Billings WZ et al. "High-Dose Inactivated Influenza Vaccine Inconsistently Improves Heterologous Antibody Responses in an Older Human Cohort," *The Journal of Infectious Diseases* 2025, jiaf003. 9 pages. https://academic.oup.com/jid/advance-article-abstract/doi/10.1093/infdis/jiaf003/7945323#google_vignette.

Black et al., "Influence of Statins on Influenza Vaccine Response in Elderly Individuals," *The Journal of Infectious Diseases* 2016, 213(8), pp. 1224-1228.

Bricout et al., "The relative effectiveness of a high-dose quadrivalent influenza vaccine versus standard-dose quadrivalent influenza vaccines in older adults in France: a retrospective cohort study during the 2021-2022 influenza season," *Clinical microbiology and Infection* 2024, 30(12), 1592-1598. https://www.sciencedirect.com/science/article/pii/S1198743X24004105#ack0010.

Caldera, F. et al., "Influenza vaccination in immunocompromised populations: Strategies to improve immunogenicity," *Vaccine 2021*, 39(1), A15-A23. https://www.sciencedirect.com/science/article/abs/pii/S0264410X20314900.

Cao W. et al., "Improving immunogenicity and effectiveness of influenza vaccine in older adults," *Expert Review of Vaccines* 2011, 10(11), pp. 1529-1537. https://www.tandfonline.com/doi/abs/10.1586/erv.11.137.

Capital Markets Day—Play to Win—Dec. 10, 2019 [PowerPoint Slides]. Sanofi. https://www.sanofi.com/assets/dotcom/content-app/events/investor-presentation/2019/Capital-Markets-Day/2019_12_10_CMD FINAL_SLIDES_WITH_APPENDICES_v3.pdf.

Cate TR, et al. "A high dosage influenza vaccine induced significantly more neuraminidase antibody than standard vaccine among elderly subjects," *Vaccine* 2010, 28(9), pp. 2076-2079. https://www.sciencedirect.com/science/article/abs/pii/S0264410X09019458?via%3Dihub.

Chahine EB, "High-Dose Inactivated Influenza Vaccine Quadrivalent for Older Adults," *Annals of Pharmacotherapy* 2021, 55(1), pp. 89-97. https://journals.sagepub.com/doi/10.1177/1060028020935645?url_ver=Z39.88-2003&rfr_id=ori:rid:crossref.org&rfr_dat=cr_pub%20%200pubmed.

Chang LJ et al. "Safety and immunogenicity of high-dose quadrivalent influenza vaccine in adults ≥65 years of age: A phase 3 randomized clinical trial," *Vaccine* 2019, 37(39), pp. 5825-5834. https://www.sciencedirect.com/science/article/pii/S0264410X19310667?via%3Dihub.

Chit, A et al. "Cost-effectiveness of high-dose versus standard-dose inactivated influenza vaccine in adults aged 65 years and older: an economic evaluation of data from a randomised controlled trial,"

*The Lancet Infectious Diseases* 2015, 15(12), pp. 1459-1466. https://www.thelancet.com/journals/laninf/article/PIIS1473-3099(15)002-19-2/abstract.

Christensen, J. et al., "Relative Effectiveness of High-Dose vs. Standard-Dose Quadrivalent Influenza Vaccine in Older Adults with Cardiovascular Disease: A Prespecified Analysis of the DANFLU-1 Randomized Clinical Trial," *Circulation: Cardiovascular Quality and Outcomes*. 10.1161/CIRCOUTCOMES.124.011496. https://www.ahajournals.org/doi/abs/10.1161/CIRCOUTCOMES.124.011496.

Clark TW et al., "Recent advances in the influenza virus vaccine landscape: a comprehensive overview of technologies and trials," *Clin Micro Biol Rev* 2024, 37, e00025-24. https://journals.asm.org/doi/abs/10.1128/cmr.00025-24.

Clements et al. "Cost-effectiveness analysis of universal influenza vaccination with quadrivalent inactivated vaccine in the United States," *Human Vaccines & Immunotherapeutics* 2014, 10(5), pp. 1171-1180.

Colmegna, I. et al., "Immunogenicity and safety of high-dose versus standard-dose inactivated influenza vaccine in rheumatoid arthritis patients: a randomised, double-blind, active-comparator trial," *The Lancet Rheumatology* 2020, 2(1), pp. e14-e23 https://www.thelancet.com/journals/lanche/article/PIIS2665-9913(19)30094-3/abstract.

Couch RB et al. "Safety and immunogenicity of a high dosage trivalent influenza vaccine among elderly subjects," *Vaccine* 2007, 25(44), pp. 7656-7663. https://www.sciencedirect.com/science/article/abs/pii/S0264410X07009681?via%3Dihub.

Curtis et al., "Live, Attenuated Varicella Zoster Vaccination of an Immunocompromised Patient," *Journal of General Internal Medicine* 2008, 23(5), pp. 648-649.

Danesh et al., "Immunomodulatory Effects of HMG-CoA Reductase Inhibitors," *Archivum Immunologiae et Therapiae Experimentalis* 2003, 51, pp. 139-148.

Debbag et al. "The Impact of Vaccination on COVID-19, Influenza, and Respiratory Syncytial Virus-Related Outcomes: A Narrative Review," *Infect. Dis. Ther.* 2025, 14(Suppl_1), pp. S63-S97. https://link.springer.com/article/10.1007/s40121-024-01079-x.

Deguchi, *Japanese Journal of Clinical and Experimental Medicine* 2004, 81(12): pp. 1938-1942.

Diaco M. et al "Introductory paper: High-dose influenza vaccine," *Vaccine* 2021, 39(1), pp. A1-A5 https://www.sciencedirect.com/science/article/pii/S0264410X20311476#bb0265.

DiazGranados C, et al. "High-dose trivalent influenza vaccine compared to standard dose vaccine in elderly adults: Safety, immunogenicity and relative efficacy during the 2009-2010 season," *Vaccine* 2013, 31(6), pp. 861-866. https://www.sciencedirect.com/science/article/abs/pii/S0264410X1201780X?via%3Dihub.

DiazGranados CA, et al. "Efficacy of High-Dose versus Standard-Dose Influenza Vaccine in Older Adults," *N Engl J Med.* 2014, 371(7), pp. 635-645. https://www.nejm.org/doi/full/10.1056/nejmoa1315727.

DiazGranados CA, et al. "Prevention of serious events in adults 65 years of age or older: A comparison between high-dose and standard-dose inactivated influenza vaccines," *Vaccine* 2015, 33(38), pp. 4988-4993. https://www.sciencedirect.com/science/article/pii/S0264410X15009342?via%3Dihub.

DiazGranados CA, et al. "Safety and immunogenicity of high-dose trivalent inactivated influenza vaccine in adults 50-64 years of age," *Vaccine* 2015, 33, pp. 7188-7193. https://www.sciencedirect.com/science/article/pii/S0264410X15015935.

DiazGranados CA, et al. "Efficacy and immunogenicity of high-dose influenza vaccine in older adults by age, comorbidities, and frailty," *Vaccine* 2015, 33(36), pp. 4565-4571.

DiazGranados CA et al. "Effect of Previous-Year Vaccination on the Efficacy, Immunogenicity, and Safety of High-Dose Inactivated Influenza Vaccine in Older Adults," *Clinical Infectious Diseases* 2016, 62(9), pp. 1092-1099 https://academic.oup.com/cid/article/62/9/1092/1745386.

Dolk, C. et al. "Cost-Utility of Quadrivalent Versus Trivalent Influenza Vaccine in Germany, Using an Individual-Based Dynamic Transmission Model," *PharmacoEconomics* 2016, 34, pp. 1299-1308.

(56) References Cited

OTHER PUBLICATIONS

Doyle, JD et al. "Relative and Absolute Effectiveness of High-Dose and Standard-Dose Influenza Vaccine Against Influenza-Related Hospitalization Among Older Adults—United States, 2015-2017," *Clinical Infectious Diseases* 2021, 72(6), pp. 995-1003. https://academic.oup.com/cid/article/72/6/995/5739665.

Dunning AJ, et al. "Correlates of Protection against Influenza in the Elderly: Results from an Influenza Vaccine Efficacy Trial," *Clin Vaccine Immunol* 2016, 23(3), pp. 228-235. https://journals.asm.org/doi/full/10.1128/cvi.00604-15.

Ertmer et al. "Estimating the Full Value of High-Dose Influenza Vaccine," *Letters to the Editor* 2017, 65(9), pp. 2110-2111. https://agsjournals.onlinelibrary.wiley.com/doi/full/10.1111/jgs.14950.

Falsey AR, et al. "Randomized, double-blind controlled phase 3 trial comparing the immunogenicity of high-dose and standard-dose influenza vaccine in adults 65 years of age and older." *J Infect Dis.* 2009, 200(2), pp. 172-180. https://academic.oup.com/jid/article/200/2/172/955522?login=true.

"FDA approves Fluzone® High-Dose Quadrivalent (Influenza Vaccine) for adults 65 years of age and older," Sanofi US News. Nov. 4, 2019. https://www.news.sanofi.us/2019-11-04-FDA-approves-Fluzone-R-High-Dose-Quadrivalent-Influenza-Vaccine-for-adults-65-years-of-age-and-older.

Felicilda-Reynaldo, RFD "Types of Flu Vaccines for Yearly Immunization," *CNE* 2014, 23(4), pp. 256-260. https://drive.google.com/file/d/1aeF5F6egbzlRBGUadDcpPAt8VclHpgz7/view.

Fiore AE et al. "Prevention and Control of Influenza with Vaccines: Recommendations of the Advisory Committee on Immunization Practices (ACIP), 2010," *Morbidity and Mortality Weekly Report* 2010, 59(RR-8), 68 pages. https://www.cdc.gov/MMWR/PREVIEW/MMWRHTML/rr5908a1.htm.

Fleming et al., "An assessment of the effect of statin use on the incidence of acute respiratory infections in England during winters 1998-1999 to 2005-2006," *Epidemiol Infect* 2010, 138(9), pp. 1281-1288.

Fluad: Product Monograph, Approved Jun. 2011.

"Fluzone® High-Dose Quadrivalent High-Dose Quadrivalent Influenza Virus Vaccine—Types A and B (Split Virion)" Product Monograph, Revised Apr. 23, 2024.

"372 Fluzone® High-Dose" Package Insert, Revised Dec. 22, 2009.

Frey et al., "Comparison of the safety and immunogenicity of an MF59®-adjuvanted with a non-adjuvanted seasonal influenza vaccine in elderly subjects," *Vaccine* 2014, 32(39), pp. 5027-5034.

Funatsu et al., "Atorvastatin (Lipitor®): a review of its pharmacological and clinical profile," *Folia Pharmacologica Japonica* 2001, 117(1), pp. 65-76.

Gaertner B.C. et al., "Importance and value of adjuvanted influenza vaccine in the care of older adults from a European perspective—A systematic review of recently published literature on real-world data," *Vaccine* 2022, 40, 2999-3008. https://www.sciencedirect.com/science/article/pii/S0264410X22004406.

Gao Z et al., "Quantification of the total neuraminidase content of recent commercially-available influenza vaccines: Introducing a neuraminidase titration reagent," *Vaccine* 2020, 38(4), pp. 715-718. https://www.sciencedirect.com/science/article/abs/pii/S0264410X19315701.

Giaquinta, S. et al., "Randomized, double-blind comparison of standard-dose vs. high-dose trivalent inactivated influenza vaccine in pediatric solid organ transplant patients," *Pediatric Transplantation* 2015, 19(2), pp. 219-228. https://onlinelibrary.wiley.com/doi/10.1111/petr.12419.

"Grade: Higher Dose and Adjuvanted Influenza Vaccines for Persons Aged ≥65 Years," CDC—Advisory Committee on Immunization Practices (ACIP), Sep. 9, 2024. Accessed Feb. 10, 2025. https://www.cdc.gov/acip/grade/influenza-older-adults.html.

Greenberg, Michael, "Making strides to help protect our most vulnerable this flu season," STAT. Undated. Accessed Feb. 11, 2025. https://www.statnews.com/sponsor/2022/09/09/making-strides-to-help-protect-our-most-vulnerable-this-flu-season/.

Greenberg, DP et al., "Safety and immunogenicity of a quadrivalent inactivated influenza vaccine compared to licensed trivalent inactivated influenza vaccines in adults," *Vaccine* 2013, 31(5), pp. 770-776. https://www.sciencedirect.com/science/article/abs/pii/S0264410X12017240?via%3Dihub.

Grohskopf, LA. et al., "Prevention and Control of Seasonal Influenza with Vaccines: Recommendations of the Advisory Committee on Immunization Practices—United States, 2013-2014," *MMWR Recomm Rep* 2013, 62(7), pp. 1-48. https://www.cdc.gov/Mmwr/preview/mmwrhtml/rr6207a1.htm.

Grohskopf, LA. et al. "Prevention and Control of Seasonal Influenza with Vaccines: Recommendations of the Advisory Committee on Immunization Practices—United States, 2016-17 Influenza Season," *MMWR Recomm Rep* 2016, 65(No. RR-5), pp. 1-32. https://www.cdc.gov/mmwr/volumes/65/rr/rr6505a1.htm.

Grohskopf et al., "Prevention and Control of Seasonal Influenza with Vaccines: Recommendations of the Advisory Committee on Immunization Practices, United States, 2021-22 Influenza Season," *Recommendations and Reports* 2021, 70(5), pp. 1-28. https://www.cdc.gov/mmwr/volumes/70/rr/rr7005a1.htm?fbclid=IwAR06XG0XO8hfvCrc4T2Unw84x9sAo5ROBYko0CbAz54hXI3Gb3UKjIW2UWQ#print.

Hakim et al., "Immunogenicity and safety of inactivated monovalent 2009 H1 N1 influenza A vaccine in immunocompromised children and young adults," *Vaccine* 2012, 30(5), pp. 879-885.

Hakim H. et al., "Immunogenicity and safety of high-dose trivalent inactivated influenza vaccine compared to standard-dose vaccine in children and young adults with cancer or HIV infection," *Vaccine* 2016, 34(27), pp. 3141-3148. https://www.sciencedirect.com/science/article/abs/pii/S0264410X16302079.

Halasa, NB et al., "Randomized Double-Blind Study of the Safety and Immunogenicity of Standard-Dose Trivalent Inactivated Influenza Vaccine versus High-Dose Trivalent Inactivated Influenza Vaccine in Adult Hematopoietic Stem Cell Transplantation Patients," *Biol. Blood Marrow Transplant* 2016, 22, pp. 528-535. https://www.sciencedirect.com/science/article/pii/S1083879115018649.

Hannoun et al., "Immunogenicity and protective efficacy of influenza vaccination," *Virus Research* 2004, 103, pp. 133-138. https://www.sciencedirect.com/science/article/abs/pii/S0168170204001248?via%3Dihub.

Hilgendorf et al., "Vaccination of allogeneic haematopoietic stem cell transplant recipients: Report from the International Consensus Conference on Clinical Practice in chronic GVHD," *Vaccine* 2011, 29(16), pp. 2825-2833.

Hitsumoto et al., "Relationship Between Insulin Resistance and Reduction in Oxidative Stress in Vivo by Atorvastatin," *J. Cardiol.* 2004, 44(6), pp. 233-242.

Hollingsworth R, et al. "Effectiveness of the quadrivalent high-dose influenza vaccine for prevention of cardiovascular and respiratory events in people aged 65 years and above: Rationale and design of a real-world pragmatic randomized clinical trial," *American Heart Journal* 2021, 237, pp. 54-61. https://www.sciencedirect.com/science/article/pii/S0002870321000727?via%3Dihub.

Højbjerg Lassen, MC. et al., "Effects of high-dose versus standard-dose quadrivalent influenza vaccine among patients with diabetes: A post-hoc analysis of the DANFLU-1 trial," *Diabetes Obes. Metab.* 2024, 26, pp. 1821-1829. https://dom-pubs.onlinelibrary.wiley.com/doi/full/10.1111/dom.15498.

Hughes K. et al., "Effectiveness of influenza vaccine for preventing laboratory-confirmed influenza hospitalizations in immunocompromised adults," *Clin Infect Dis.* 2021, 73(11), pp. e4353-e4360. doi: 10.1093/cid/ciaa1927. https://academic.oup.com/cid/article/73/11/e4353/6060064?login=true#google_vignette.

"Influenza Vaccine for 2022-2023," *Med Lett Drugs Ther.* 2022, 64(1660), pp. 153-158. http://www.medletter.com/TML-article-1660a.

"Influenza Vaccine for 2023-2024," *Med Lett Drugs Ther.* 2023, 65(1687), pp. 161-166. https://liqweb.medicalletter.org/TML-article-1687a.

Influvac® 2012 Label.

Innovation to drive sustainable growth in Vaccines—Part 1—Vaccines Investor Event [PowerPoint Slides]. Sanofi. Jun. 29, 2023.

(56)            References Cited

OTHER PUBLICATIONS https://www.sanofi.com/assets/dotcom/content-app/events/investor-presentation/2023/vaccines-investor-event/presentation-vaccines-event-2023.pdf.

International Search Report for International Application No. PCT/IB2015/057388, mailed Dec. 17, 2015.

Izikson, R. et al. "Safety and immunogenicity of a high-dose quadrivalent influenza vaccine administered concomitantly with a third dose of the mRNA-1273 SARS-CoV-2 vaccine in adults aged 65 years: a phase 2, randomised, open-label study," *The Lancet Respiratory Medicine* 2022, 10(4) pp. 392-402.

Izurieta HS et al. "Comparative effectiveness of high-dose versus standard-dose influenza vaccines in US residents aged 65 years and older from 2012 to 2013 using Medicare data: a retrospective cohort analysis," *Lancet Infect. Dis.* 2015, 15, pp. 293-300. https://www.thelancet.com/journals/laninf/article/PIIS1473-3099(14)71087-4/abstract.

Jin XW et al., "2012-2013 Influenza update: Hitting a rapidly moving target," *Cleveland Clinic Journal of Medicine* 2012, 79(11), pp. 777-784. https://web.archive.org/web/20190309091419id_/http://pdfs.semanticscholar.org/f6e1/307ebe028860825447a463eb6c2a308583f3.pdf.

Ji-Young, You. "Solid organ transplant patients aged 18-64 need high-immunogenic influenza vaccination," *Korea Biomedical Review* 2024, 3 pages. https://www.koreabiomed.com/news/articleView.html?idxno=24903.

Johansen, N.D. et al., "A Pragmatic Randomized Feasibility Trial of Influenza Vaccines," *NEJM Evid* 2023, 2(2), 11 pages. DOI: 10.1056/EVIDoa2200206 https://evidence.nejm.org/doi/full/10.1056/EVIDoa2200206.

Johansen ND et al., "Effectiveness of high-dose versus standard-dose quadrivalent influenza vaccine against recurrent hospitalizations and mortality in relation to influenza circulation: A post-hoc analysis of the DANFLU-1 randomized clinical trial," *Clinical Microbiology and Infection* 2024, 30(11), pp. 1453-1459. https://www.sciencedirect.com/science/article/pii/S1198743X24000399.

Keitel WA et al. "Safety of High Doses of Influenza Vaccine and Effect on Antibody Responses in Elderly Persons," *Arch Intern Med.* 2006, 166(10), pp. 1121-1127. https://jamanetwork.com/journals/jamainternalmedicine/fullarticle/410359.

Keitel et al., "Dose ranging of adjuvant and antigen in a cell culture H5N1 influenza vaccine: Safety and immunogenicity of a phase 1/2 clinical trial," *Vaccine* 2010, 28(10), pp. 840-848.

Kono et al., "Study on Therapeutic Equivalence of Generic Drug (Simvastatin) Based on Retrospective Usage Survey," *Jpn. J. Pharm. Health Care Sci.* 2006, 32(11), pp. 1152-1158.

Kramer, KL, "Seasonal Influenza Vaccination: Understanding Vaccine Effectiveness in Immunocompromised Adults," University of Pittsburgh ProQuest Dissertations & Theses, 2022. 31095247. https://www.proquest.com/openview/1d600cad261ca0c35b0243b2182ef657/1?pq-origsite=gscholar&cbl=18750&diss=y.

Kwong et al., "Influenza Morbidity and Mortality in Elderly Patients Receiving Statins: A Cohort Study", *PLoS One* 2009, 4(11), e8087.

Lai JJ et al. "Alternative-Dose versus Standard-Dose Trivalent Influenza Vaccines for Immunocompromised Patients: A Meta-Analysis of Randomised Control Trials," *J. Clin. Med.* 2019, 8(5), 590. 15 pages. https://www.mdpi.com/2077-0383/8/5/590.

Lee et al., "Short-term atorvastatin treatment enhances specific antibody production following tetanus toxoid vaccination in healthy volunteers," *Vaccine* 2006, 24(19), pp. 4035-4040.

Lee JKH et al. "Efficacy and effectiveness of high-dose influenza vaccine in older adults by circulating strain and antigenic match: An updated systematic review and meta-analysis," Vaccine 2021, 39, pp. A24-A35. https://doi.org/10.1016/j.vaccine.2020.09.004. https://www.sciencedirect.com/science/article/pii/S0264410X20311464?via%3Dihub.

Lee, JKH et al., "High-dose influenza vaccine in older adults by age and seasonal characteristics: Systematic review and meta-analysis update," *Vaccine: X*, 2023, 100327. 7 pages. https://www.sciencedirect.com/science/article/pii/S2590136223000682#bb0020.

L'huillier AG et al., "Cell-Mediated Immune Responses After Influenza Vaccination of Solid Organ Transplant Recipients: Secondary Outcomes Analyses of a Randomized Controlled Trial," *The Journal of Infectious Disease* 2020, 221, pp. 53-62. https://academic.oup.com/jid/article/221/1/53/5573328.

Liu WM et al., "Aging and impaired immunity to influenza viruses: Implications for vaccine development," *Human Vaccines* 2011, 7(sup1), pp. 94-98. https://www.tandfonline.com/doi/abs/10.4161/hv.7.0.14568.

Long, CB et al., "Humoral and Cell-Mediated Immune Responses to Monovalent 2009 Influenza A/H1N1 and Seasonal Trivalent Influenza Vaccines in High-Risk Children," *The Journal of Pediatrics* 2012, 160(1), pp. 74-81. https://www.sciencedirect.com/science/article/abs/pii/S002234761100672X.

Mach, "Immunosuppressive effects of statins," *Atherosclerosis Supplements* 2002, 3, pp. 17-20.

Manley, HJ et al. "Seroresponse to Inactivated and Recombinant Influenza Vaccines Among Maintenance Hemodialysis Patients," *American Journal of Kidney Disease* 2022, 80(3) pp. 309-318. https://www.sciencedirect.com/science/article/abs/pii/S0272638622005273.

McGrath, LJ et al. "High-dose influenza vaccine use among patients receiving hemodialysis in the United States, 2010-2013," *Vaccine* 2018, 36, pp. 6087-6094. https://www.sciencedirect.com/science/article/abs/pii/S0264410X18312295.

McLean et al., "Effect of Statin Use on Influenza Vaccine Effectiveness," *The Journal of Infectious Diseases* 2016, 214, pp. 1150-1158.

McManus M. et al. "Safety of high dose trivalent inactivated influenza vaccine in pediatric patients with acute lymphoblastic leukemia," *Pediatric Blood & Cancer* 2014, (61)5, pp. 815-820. https://onlinelibrary.wiley.com/doi/abs/10.1002/pbc.24863.

"Media Update: Survey: Physicians and pharmacists would tell CDC to recommend vaccine like Fluzone High-Dose Quadrivalent (Influenza Vaccine) for people 65 years and older," *Sanofi* 2022. https://www.sanofi.com/en/media-room/press-releases/2022/2022-06-22-12-00-00-2467035.

Mehrbod et al., "Mechanisms of Action and Efficacy of Statins against Influenza," BioMed Research International (2014).

Miskulin, DC et al. "High-Dose Seasonal Influenza Vaccine in Patients Undergoing Dialysis," *Clinical Journal of the American Society of Nephrology* 2018, 13(11), pp. 1703-1711. https://journals.lww.com/cjasn/abstract/2018/11000/high_dose_seasonal_influenza_vaccine_in_patients.15.aspx.

Mombelli, M et al., "Immunogenicity and safety of double versus standard dose of the seasonal influenza vaccine in solid-organ transplant recipients: A randomized controlled trial," *Vaccine* 2018, 36, pp. 6163-6169. https://www.sciencedirect.com/science/article/abs/pil/S0264410X18311861.

Monto, AS et al., "Influenza control in the 21st century: Optimizing protection of older adults," *Vaccine* 2009, 27(37), pp. 5043-5053. https://www.sciencedirect.com/science/article/abs/pii/S0264410X09008810.

Moro PL, et al. "Postlicensure safety surveillance for high-dose trivalent inactivated influenza vaccine in the Vaccine Adverse Event Reporting System Jul. 1, 2010-Dec. 31, 2010," *Clin Infect Dis.* 2012, 54, pp. 1608-1614. https://academic.oup.com/cid/article-abstract/54/11/1608/323144?redirectedFrom=fulltext&login=true#google_vignette.

Natori, Y. et al., "A Double-Blind, Randomized Trial of High-Dose vs Standard-Dose Influenza Vaccine in Adult Solid-Organ Transplant Recipients," *Clinical Infectious Diseases* 2018, 66(11), pp. 1698-1704.

Net, P. et al., "Estimating public health and economic benefits along 10 years of Fluzone® High Dose in the United States," *Vaccine* 2021, 39(Supplement 1), pp. A56-A69. https://www.sciencedirect.com/science/article/pii/S0264410X21000207.

Ohfuji et al., "Target groups for influenza vaccination," *Nihon Koshu Eisei Zasshi* 2007, 54(6), pp. 361-367.

Okazaki et al., "Immunomodulatory activities of statins," *Nihon Rinsho Meneki Gakkai Kaishi* 2004, 27(6), pp. 357-360.

Okoli, GN et al., "Characteristics and methodological standards across systematic reviews with Meta-analysis of efficacy and/or

(56) References Cited

OTHER PUBLICATIONS effectiveness of influenza vaccines: an overview of reviews," *Infectious Diseases* 2022, 54(12), pp. 861-880. https://www.tandfonline.com/doi/full/10.1080/23744235.2022.2114537?needAccess=true.

Optaflu® 2012 Label.

Packard et al., "Atorvastatin treatment and vaccination efficacy," *J. Clin. Pharmacol.* 2007, 47(8), pp. 1022-1027.

Parodi et al., "Inactivated influenza vaccines: recent progress and implications for the elderly," *Drugs Aging* 2011, 28(2), pp. 93-106.

Pepin et al., "Immunogenicity and safety of a quadrivalent high-dose inactivated influenza vaccine compared with a standard-dose quadrivalent influenza vaccine in healthy people aged 60 years or older: a randomized Phase III trial," *Human Vaccines & Immunotherapeutics* 2021, 17(12), pp. 5475-5486. https://www.tandfonline.com/doi/full/10.1080/21645515.2021.1983387#d1e290.

Prada et al. "Influenza B Lineages Have More in Common Than Meets the Eye. Trivalent Influenza Vaccines Trigger Heterotypic Antibodies Against Both Influenza B Viruses," *Frontier in Microbiology* 2021, 12(737216). 12 pages. https://www.frontiersin.org/journals/microbiology/articles/10.3389/fmicb.2021.737216/full.

Q3 2021 Results—Play to Win—Oct. 28, 2021 [PowerPoint Slides]. Sanofi. https://www.sanofi.com/assets/dotcom/content-app/publications/quarterly-financial-reports/2021-q3-financial-results-en.pdf.

Q3 2024 Results—Play to Win—Oct. 25, 2024 [PowerPoint Slides]. Sanofi. https://www.sanofi.com/assets/dotcom/content-app/events/quaterly-results/2024/2024-q3-2024-results/q3-2024-presentation-en.pdf.

Rainsford, "Review: Influenza ('Bird Flu'), inflammation and anti-inflammatory/analgesic drugs," *Inflammopharmacology* 2006, 14, pp. 2-9.

"Recommended composition of influenza virus vaccines for use in the 2012-2013 northern hemisphere influenza season," WHO—Global Influenza Programme, Feb. 2012, 16 pages. https://www.who.int/publications/m/item/recommended-composition-of-influenza-virus-vaccines-for-use-in-the-2012-2013-northern-hemisphere-influenza-season#:~:text=It%20is%20recommended%20that%20vaccines,1%2F2010%2Dlike%20virus.

Redondo, E. et al. "Cost-utility analysis of influenza vaccination in a population aged 65 years or older in Spain with a high-dose vaccine versus an adjuvanted vaccine," *Vaccine* 2021, 39(36), pp. 5138-5145. https://www.sciencedirect.com/science/article/pii/S0264410X21009269.

Reed C, et al. "Public health impact of including two lineages of influenza B in a quadrivalent seasonal influenza vaccine," *Vaccine* 2012, 30, pp. 1993-1998. https://www.sciencedirect.com/science/article/abs/pii/S0264410X11020470?via%3Dihub.

"Respiratory Tract Infections: Advances in Research and Treatment," Edited by A. Acton, 2011.

Richardson DM, et al. "Comparative effectiveness of high-dose versus standard-dose influenza vaccination in community-dwelling veterans," *Clin Infect Dis.* 2015, 61, pp. 171-176. https://academic.oup.com/cid/article/61/2/171/329279.

Robertson, CA. et al., "Fluzone® high-dose influenza vaccine," *Expert Rev. Vaccines* 2016, 15(12), pp. 1495-1505. https://www.tandfonline.com/doi/full/10.1080/14760584.2016.1254044#abstract.

Rubin LG et al. "2013 IDSA clinical practice guideline for vaccination of the immunocompromised host." *Clin Infect Dis* 2014, 58(3), pp. e44-100. https://academic.oup.com/cid/article/59/1/144/405127.

Saku et al., "Randomized Head-to-Head Comparison of Pitavatatin, Atorvastatin, and Rosuvastatin for Safety and Efficacy (Quantity and Quality of LDL)," *Circulation Journal* 2011, 75(6), pp. 1493-1505.

Samson SI, et al. "Immunogenicity of high-dose trivalent inactivated influenza vaccine: a systematic review and meta-analysis," *Expert Review of Vaccines* 2019, 18(3), pp. 295-308. https://www.tandfonline.com/doi/abs/10.1080/14760584.2019.1575734.

Sanchez, L. et al., "Immunogenicity and safety of high-dose quadrivalent influenza vaccine in Japanese adults ≥65 years of age: a randomized controlled clinical trial," *Human Vaccines & Immunotherapeutics* 2020, 16(4), pp. 858-866. https://www.tandfonline.com/doi/full/10.1080/21645515.2019.1677437#abstract.

Sanchez, L. et al. "Superior immunogenicity of high-dose quadrivalent inactivated influenza vaccine versus Standard-Dose vaccine in Japanese Adults ≥ 60 years of age: Results from a phase III, randomized clinical trial," *Vaccine* 2023, 41(15), pp. 2553-2561. https://www.sciencedirect.com/science/article/pii/S0264410X23002256#bb0060.

"Sanofi: Q4 sales growth of 10.3%, 2024 business EPS guidance exceeded, and strong business EPS rebound expected in 2025," Sanofi Press Release. Jan. 30, 2025. https://www.sanofi.com/assets/dotcom/pressreleases/2025/2025-01-30-06-30-00-3017713-en.pdf.

Schlienger et al., "Statins and the Risk of Pneumonia: A Population-Based, Nested Case-Control Study," *Pharmacotherapy* 2007, 27(3), pp. 325-332.

Shay, DK et al., "Comparative Effectiveness of High-Dose Versus Standard-Dose Influenza Vaccines Among US Medicare Beneficiaries in Preventing Postinfluenza Deaths During 2012-2013 and 2013-2014," *The Journal of Infectious Diseases* 2017, 215(4), pp. 510-517. https://academic.oup.com/jid/article/215/4/510/3058746#google_vignette.

Song, JY. et al., "Long-term immunogenicity of influenza vaccine among the elderly: Risk factors for poor immune response and persistence," *Vaccine* 2010, 28(23), pp. 3929-3935. https://www.sciencedirect.com/science/article/abs/pii/S0264410X10004676.

Stojanovic et al., "Survival, graft atherosclerosis, and rejection incidence in heart transplant recipients treated with statins: 5-year follow-up," *J. Heart Lung Transplant* 2005, 24(9), pp. 1235-1238.

Sugaya, *Journal of Pediatric Practice* 2004, 67(11), pp. 1913-1918.

Sullivan SJ., et al., "Advances in the vaccination of the elderly against influenza: role of a high-dose vaccine," *Expert Rev. Vaccines* 2010, 9(10), pp. 1127-1133. https://www.tandfonline.com/doi/full/10.1586/erv.10.117?needAccess=true.

Sullivan SG, et al., "Burden, effectiveness and safety of influenza vaccines in elderly, paediatric and pregnant populations," *Therapeutic Advances in Vaccines and Immunotherapy* 2019, 7, 16 pages. https://journals.sagepub.com/doi/10.1177/2515135519826481.

Torbic, H. et al., "Current Influenza Vaccine Options for 2014," *Curr Emerg Hosp Med Rep* 2015, 3, pp. 126-133. https://link.springer.com/article/10.1007/s40138-015-0077-7#citeas.

Tristano et al., "Immunomodulatory effects of statins and autoimmune rheumatic diseases: novel intracellular mechanism involved," *Int Immunopharmacol* 2006, 6(12), pp. 1833-1846.

Tsang, P. et al., "Immunogenicity and safety of Fluzone® intradermal and high-dose influenza vaccines in older adults ≥65 years of age: A randomized, controlled, phase II trial," *Vaccine* 2014, 32(21), pp. 2507-2517. https://www.sciencedirect.com/science/article/pii/S0264410X13013583.

Vaccines Investor Event—Part 1—Growing current business [PowerPoint Slides]. Sanofi. Dec. 1, 2021. https://www.sanofi.com/assets/dotcom/content-app/events/investor-presentation/2021/vaccines-investor-event/20211201_Sanofi_Vaccines_Investor_Event_Part_1_vFinal.pdf.

Vaccines Investor Event—Part 2—Growing current business [PowerPoint Slides]. Sanofi. Dec. 1, 2021. https://www.sanofi.com/assets/dotcom/content-app/events/investor-presentation/2021/vaccines-investor-event/20211201_Sanofi_Vaccines_Investor_Event_Part_2_vFinal.pdf.

Van Buynder, P. "Enhancing influenza vaccination in older people," *Medicine Today* 2019, 20(2 Suppl), pp. 6-10. https://medicinetoday.com.au/mt/2019/february/supplements/feature-article/enhancing-influenza-vaccination-older-people.

Vandermeer et al., "Association Between Use of Statins and Mortality Among Patients Hospitalized With Laboratory-Confirmed Influenza Virus Infections: A Multistate Study," *The Journal of Infectious Diseases* 2012, 205, pp. 13-19.

Vardeny, et al. "Effect of High-Dose Trivalent vs Standard-Dose Quadrivalent Influenza Vaccine on Mortality or Cardiopulmonary Hospitalization in Patients With High-risk Cardiovascular Dis-

(56)            References Cited

OTHER PUBLICATIONS ease—A Randomized Clinical Trial," *JAMA* 2021, pp. E1-E11. https://jamanetwork.com/journals/jama/fullarticle/2773989.

Weissman et al. "Clinical efficacy and safety of high dose trivalent influenza vaccine in adults and immunosuppressed populations—A systematic review and meta-analysis," *J. Infect.* 2021, 83(4), pp. 444-451. https://www.journalofinfection.com/article/S0163-4453(21)00417-5/abstract.

Yokote et al., "Safety of Attenuated Smallpox Vaccine LC16m8 in Immunodeficient Mice," *Clinical and Vaccine Immunology* 2014, 21(9), pp. 1261-1266.

Young-Xu et al. "Relative Vaccine Effectiveness of High-Dose Versus Standard-Dose Influenza Vaccines Among Veterans Health Administration Patients," *The Journal of Infectious Diseases* 2018, 217, pp. 1718-1727.

Young-Xu et al. "Analysis of relative effectiveness of high-dose versus standard-dose influenza vaccines using an instrumental variable method," *Vaccine* 2019, 37 (11), pp. 1484-1490. https://www.sciencedirect.com/science/article/pii/S0264410X19301483.

Zeevat, F. et al. "Cost-Effectiveness of Quadrivalent Versus Trivalent Influenza Vaccination in the Dutch National Influenza Prevention Program," *Value Health* 2021, 24(1), pp. 3-10.

Zeevat et al. "Reducing Hospital Capacity Needs for Seasonal Respiratory Infections: The Case of Switching to High-Dose Influenza Vaccine for Dutch Older Adults," *Value Health* 2023, 26(4), pp. 461-464. https://www.sciencedirect.com/science/article/pii/S1098301522047544#bbib7.

Zeevat, F. et al. "Assessment of vaccination policies from a health economic perspective: opportunities and emerging foci" [Thesis fully internal (DIV), University of Groningen]. University of Groningen. 2023. 223 pages. https://research.rug.nl/en/publications/assessment-of-vaccination-policies-from-a-health-economic-perspec.

Black, S. et al., "Hemagglutination inhibition antibody titers as a correlate of protection for inactivated influenza vaccines in children," *Pediatr. Infect. Dis. J.* 2011, 30(12), pp. 1081-1085.

Bosaeed, M. et al., "Seasonal influenza vaccine in immunocompromised persons," *Human Vaccines & Immunotherapeutics* 2018, 14(6), pp. 1311-1322.

Treanor, J. J. et al., "Safety and Immunogenicity of an Inactivated Subvirion Influenza A (H5N1) Vaccine," *N. Engl. J. Med.* 2006, 354(13), pp. 1343-1351.

Wutzler, P. et al., "Targeted Vaccine Selection in Influenza Vaccination," *Dtsch Arztebl Int.* 2013, 110(47), pp. 793-798.

McKittrick et al., "Improved Immunology With High-Dose Seasonal Influenza Vaccine in HIV-Infected Persons," Annals of Internal Medicine (2013).

\* cited by examiner

VACCINATION OF IMMUNOCOMPROMISED SUBJECTS

This is a continuation of application Ser. No. 18/935,840, filed Nov. 4, 2024, which is a continuation of application Ser. No. 18/746,583, filed Jun. 18, 2024, which is a continuation of application Ser. No. 18/394,260, filed Dec. 22, 2023, which is a continuation of application Ser. No. 18/232, 504, filed Aug. 20, 2023, which is a continuation of application Ser. No. 18/188,587, filed Mar. 23, 2023, which is a continuation of application Ser. No. 18/053,496, filed Nov. 8, 2022, which is a continuation of application Ser. No. 17/854,942, filed Jun. 30, 2022, which is a continuation of Application No. 16/901, 185, filed Jun. 15, 2020 (now U.S. Pat. No. 11,406,701), which is a continuation of application Ser. No. 16/739,358, filed Jan. 10, 2020 (now U.S. Pat. No. 10,716,844), which is a continuation of application Ser. No. 15/514,154, filed Mar. 24, 2017, which is a national stage filing under 35 U.S.C. § 371 of International Application No. PCT/IB2015/057388, filed on Sep. 25, 2015, which claims priority of European Patent Application No. 14192174.2, filed on Nov. 6, 2014, and U.S. Provisional Application No. 62/149,351, filed on Apr. 17, 2015, and U.S. Provisional Application No. 62/056,019, filed Sep. 26, 2014, the entire contents of which are incorporated herein by reference.

FIELD OF THE INVENTION

The present disclosure generally relates to enhancing an immune response in individuals immunocompromised by medications or for other reasons.

BACKGROUND OF THE INVENTION

Immunosuppression induced by drugs or other reasons in a subject is an obstacle to achieving effective vaccination of the subject. It is important to note that individuals may be immunocompromised for a variety of reasons, including, for example, disease or disorder associated with immunosuppression, age (e.g., the elderly), and being on medications or medical procedures that suppress or otherwise interfere with their immune response.

Certain drugs have been implicated in causing immunomodulation in patients, including statins, non-steroidal anti-inflammatory drugs (NSAIDs), interferons, and certain antipsychotic drugs, such as clozapine and haloperidol. Such immunomodulatory effects include adverse or unwanted immunosuppression in the patients, particularly those on a long-term therapeutic regimen.

Statins are a class of drugs used to lower cholesterol levels by inhibiting the enzyme HMG-CoA reductase. Because of the association between elevated cholesterol levels and the risk of cardiovascular disease and because of studies showing that statins can lower this risk, statins have been given to large numbers of individuals, mostly older adults (Lewington S, Whitlock G, Clarke R, Sherliker P, Emberson J, Halsey J, Qizilbash N, Peto R, Collins R. (2007) "Blood cholesterol and vascular mortality by age, sex, and blood pressure: a meta-analysis of individual data from 61 prospective studies with 55,000 vascular deaths." Lancet 370 (9602): 1829-39). Although the primary goal of statin therapy has been to lower cholesterol, it has been recognized that this drug class has other effects including immunomodulatory and anti-inflammatory effects (Jain, M. K., & Ridker, P. M. (2005) "Anti-inflammatory effects of statins: clinical evidence and basic mechanisms." Nature Reviews Drug Discovery, 4(12): 977-987).

Secondary effects of a statin therapy on individuals, including both elderly and non-elderly populations, have been somewhat controversial in the literature, although most studies have concluded that statin can elicit immunomodulatory effects and that such effects are complex.

Non-steroidal anti-inflammatory drugs (NSAIDs) are a class of drugs that provides analgesic (pain-killing) and antipyretic (fever-reducing) effects, and, in higher doses, anti-inflammatory effects. NSAIDs are sometimes also referred to as nonsteroidal anti-inflammatory agents/analgesics (NSAIAs) or nonsteroidal anti-inflammatory medicines (NSAIMs). Due to the importance of pain management, the use of NSAIDs has increased dramatically in recent decades. However, all NSAIDs have the potential for certain adverse effects, including potentially unwanted suppression of an immune response.

Interferons (IFNs) are a group of signaling proteins made and released by host cells in response to the presence of pathogens, such as viruses, bacteria, parasites, or tumor cells. In a typical scenario, a virus-infected cell will release interferons causing nearby cells to heighten their anti-viral defenses. Interferon beta-1a and interferon beta-1b are used to treat and control multiple sclerosis, an autoimmune disorder. This treatment is effective for reducing attacks in relapsing-remitting multiple sclerosis and slowing disease progression and activity in secondary progressive multiple sclerosis.

The most frequent adverse effects reported by patients receiving interferon therapy are flu-like symptoms: increased body temperature, feeling ill, fatigue, headache, muscle pain, convulsion, dizziness, hair thinning, and depression. Erythema, pain and hardness on the spot of injection are also frequently observed. IFN therapy causes immunosuppression, in particular through neutropenia and can result in some infections manifesting in unusual ways. IFN therapy may also exhibit increased susceptibility to secondary infections following a viral infection, such as influenza. In such cases, the patient co-infected with the primary pathogen (such as influenza virus) and a secondary pathogen (such as a bacterial infection) may be at elevated risk of developing complication from the secondary infection.

Certain antipsychotic compounds have been reported to cause side effects including immunosuppression in subjects.

Interferon therapy is used (in combination with chemotherapy and radiation) as a treatment for some cancers.[26] This treatment can be used for treating hematological malignancy; leukemia and lymphomas including hairy cell leukemia, chronic myeloid leukemia, nodular lymphoma, and cutaneous T-cell lymphoma.[26] Patients with recurrent melanomas receive recombinant IFN-α2b.[27] Both hepatitis B and hepatitis C are treated with IFN-α, often in combination with other antiviral drugs.[28][29] Some of those treated with interferon have a sustained virological response and can eliminate hepatitis virus. The most harmful strain—hepatitis C genotype I virus—can be treated with a 60-80% success rate with the current standard-of-care treatment of interferon-α, ribavirin and recently approved protease inhibitors such as Telaprevir (Incivek) May 2011, Boceprevir (Victrelis) May 2011 or the nucleotide analog polymerase inhibitor Sofosbuvir (Sovaldi) December 2013 [30]. Biopsies of patients given the treatment show reductions in liver damage and cirrhosis. Some evidence shows giving interferon immediately following infection can prevent chronic hepatitis C, although diagnosis early in infection is difficult since physical symptoms are sparse in early hepatitis C infection. Control of chronic hepatitis C by IFN is associated with reduced hepatocellular carcinoma.[31]

Interferon treatment was evaluated in individuals suffering from herpes simplex virus epithelial keratitis. Topical interferon therapy was shown to be an effective treatment, especially with higher concentrations.[32] Interferon, either used alone or in combination with debridement, appears to be as effective as a nucleoside antiviral agent.[32] The combination of interferon and another nucleoside antiviral agent may speed the healing process.[32]

When used in the systemic therapy, IFNs are mostly administered by an intramuscular injection. The injection of IFNs in the muscle or under skin is generally well tolerated. The most frequent adverse effects are flu-like symptoms: increased body temperature, feeling ill, fatigue, headache, muscle pain, convulsion, dizziness, hair thinning, and depression. Erythema, pain and hardness on the spot of injection are also frequently observed. IFN therapy causes immunosuppression, in particular through neutropenia and can result in some infections manifesting in unusual ways. [33]

To date, there has been no consensus in the art as to the interplay between the pharmacokinetics of these drugs and their modulatory effects on various aspects of immune function in vivo and how such effects should be taken into consideration in the overall management of health in patients.

SUMMARY OF THE INVENTION

It has now been found that certain vaccine compositions and/or vaccine regimens can be effectively used to enhance a desirable immune response in an individual whose immune system is compromised. In particular, the present invention includes the recognition that a patient population on certain therapies, such as statin therapy, shows reduced immunogenicity to a vaccine, and that the use of an adjuvanted vaccine (e.g., vaccines formulated with an oil-in-water adjuvant) and/or a high-dose antigen may restore or even enhance an immune response to such a vaccine.

In a broad sense, the present invention describes immunization of a subject whose immune system is compromised for one or more reasons. Accordingly, the invention provides methods for immunizing certain target populations, including recipients of an immunomodulatory therapy (e.g., medications), such as statin therapy, NSAID therapy, interferon therapy, and/or antipsychotics therapy, by administration of a vaccine composition that is (i) adjuvanted, and/or (ii) containing a high dose antigen, to the subject in an effective amount, so that, as compared to an equivalent unadjuvanted or standard-dose vaccine, the subject elicits a better immune response to the same antigen(s) contained in the vaccine. According to the invention, the methods described herein may provide particularly beneficial immune protection to those subjects who do not otherwise produce a desired immune response to a vaccine due to medications that cause adverse immunosuppression.

Accordingly, the present invention is suitable for vaccinating subjects considered to be "at-risk." In some embodiments, the at-risk criteria include but are not limited to Individuals with confirmed medical history of any of the following: endocrine disorders, chronic cardiovascular diseases, chronic pulmonary diseases, chronic renal or hepatic diseases, neurological and neurodevelopmental conditions, blood disorders, metabolic disorders, weakened immune system, obesity, receipt of long term aspirin therapy and/or any of the therapies listed above. In some embodiments, at-risk subjects are characterized in that they are more susceptible to developing secondary infection following a primary infection and that they are at higher risk of developing complications due to the co-infections (i.e., the primary and the secondary infections). Without wishing to be bound by a particular theory, it is contemplated that a primary infection, such as influenza infection, may render the person more susceptible to a secondary infection due to immunosuppression. As a result, the subject may develop the secondary infection that is atypically severe. In some embodiments, the secondary infection is a bacterial infection, e.g., respiratory infection, skin infection, etc. The invention thus aims to counter such immunosuppressive effects by the use of protective influenza vaccines comprising an adjuvant, high dose antigens, or combination thereof, which in turn may boost the subjects' immune system to fight against the secondary infection more effectively. Thus, in some embodiments, better protection against an influenza infection in an at-risk subject provides lesser probability of the subject developing complication from a secondary infection.

In some embodiments, the invention provides methods for administering an influenza vaccine to an at-risk subject in an amount effective to elicit a protective immune response to the vaccine antigen(s). Preferably, such influenza vaccine is an adjuvanted vaccine. In situations where a subject receives multiple doses of influenza immunization (e.g., a priming dose and a booster dose), it is possible to administer an adjuvanted influenza vaccine in one dose or more, in any order. For example, a priming dose may be unadjuvanted, while a subsequent booster dose may be adjuvanted, or vice versa.

In some embodiments, the invention provides methods for administering an influenza vaccine to a subject receiving an immunosuppression-causing therapy (e.g., a statin therapy, an NSAID therapy, interferon therapy, antipsychotics therapy, etc.) in an amount effective to elicit a protective immune response to the vaccine antigen(s). Preferably, such influenza vaccine is an adjuvanted vaccine. In situations where a subject receives multiple doses of influenza immunization (e.g., a priming dose and a booster dose), it is possible to administer an adjuvanted influenza vaccine in one dose or more, in any order. For example, a priming dose may be unadjuvanted, while a subsequent booster dose may be adjuvanted, or vice versa.

The invention further provides related vaccine compositions for use in a method for enhancing an immune response in subjects, including those who are on an immunosuppression-causing therapy (e.g., a statin therapy, an NSAID therapy, interferon therapy, antipsychotics therapy, etc.). In some embodiments of the invention, such vaccine compositions are formulated with an adjuvant. Preferred adjuvants include oil-in-water emulsion-based adjuvants, such as those comprising squalene. Additionally or alternatively, vaccine compositions of the present invention may comprise a high-dose antigen, a standard-dose antigen, or a low-dose antigen. Related kits are also described.

The invention also provides a flu vaccine for a statin-treated patient, in particular an adjuvanted or high-dose flu vaccine for a statin-treated patient, preferably a patient treated with a synthetic statin. In some embodiments, the patient is 65 years or older. In alternative embodiments, the patient is under 65, but 18 years or older (i.e., between the age of 18 and 64).

The invention includes a flu vaccine for use in a statin-treated patient, in particular an adjuvanted or high dose flu vaccine for use in a statin-treated patient, preferably a patient treated with a synthetic statin. In some embodiments, the patient is 65 years or older. In alternative embodiments, the patient is under 65, but 18 years or older (i.e., between the age of 18 and 64).

The invention further includes a flu vaccine for prevention of flu in an at-risk subject, such as a statin-treated patient, in particular an adjuvanted or high dose flu vaccine for prevention of flu in a statin-treated patient, preferably a patient treated with a synthetic statin. In some embodiments, the patient is 65 years or older. In alternative embodiments, the patient is below 65, but 18 years or older (i.e., between the age of 18 and 64).

The invention also provides a composition of the invention for use as a medicament, and provides the use of a composition of the invention for the manufacture of a medicament for raising an immune response in a subject who is statin-treated, preferably a patient treated with a synthetic statin. In some embodiments, the patient is 65 years or older. In alternative embodiments, the patient is under 65, but 18 years or older (i.e., between the age of 18 and 64).

The invention further provides a method for manufacturing an adjuvanted or high-dose flu vaccine, whereby the following steps are conducted: a flu virus is grown in eggs or in a suitable cell line; the virus is harvested and purified, optionally the virus is split and the antigens are isolated; optionally the virus or the antigens are formulated and filled as a final vaccines, whereby the vaccine is for use in a statin-treated patient, preferably a patient treated with a synthetic statin. In some embodiments, the patient is 65 years or older. In alternative embodiments, the patient is under 65, but 18 years or older (i.e., between the age of 18 and 64).

When adjuvants are used in combination with flu antigens herein, the antigen component and the adjuvant component of the vaccine may be premixed, or alternatively, may be presented in separate containers for mixing by the end-user/health care provider before administration. The antigen component and the adjuvant component may be produced in the same production site or in different production sites. One aspect of the invention is the use of the antigen component(s) for formulation and/or packaging into a kit with an adjuvant component, wherein the kit is for use in patients who are statin-treated, preferably patients treated with a synthetic statin. Another aspect of the invention is the use of the adjuvant component for formulation and/or packaging into a kit with an antigen component for use in at-risk patients, such as those who are statin-treated, preferably patients treated with a synthetic statin. In some embodiments, the patient is 65 years or older. In alternative embodiments, the patient is below 65, but 18 years or older (i.e., between the age of 18 and 64).

DETAILED DESCRIPTION OF CERTAIN EMBODIMENTS

A number of factors can cause impairment of one or more aspects of immune function in a subject, rendering the subject to be immunocompromised. Certain medications, such as statins, NSAIDs, interferons, and antipsychotics, are known to cause unwanted immune modulations. In the context of the present disclosure, the phrase "an immuno-suppression-causing therapy" refers to a medical intervention or treatment that is associated with side effects characterized by unwanted immunosuppressive effects. Non-limiting examples of such therapies include a statin therapy, an NSAID therapy, interferon therapy, antipsychotics therapy, etc.

Statins are a class of drugs used to treat hypercholesterolemia and are frequently used to reduce the risk of cardiovascular disease. However, statins have been reported to exert certain immunomodulatory effects which could impact vaccine response in those who are on a statin therapy, including influenza vaccines. Similarly, other drugs widely administered for treating or alleviating certain conditions are also associated with immunosuppressive side effects.

As further detailed herein, immunogenicity measurements of adjuvanted versus unadjuvanted influenza vaccine obtained from individuals who are either on or off statin therapy have revealed significant immunosuppressive effects of statin in those receiving statin, as compared to control individuals not receiving statin therapy. As further demonstrated below (see the EXEMPLIFICATION section below), this immunosuppressive effect of statins on vaccine immune response is particularly dramatic in individuals on synthetic statins. These effects are seen in both the adjuvanted and unadjuvanted vaccine groups. Strikingly, however, the negative impact of statin therapy on a vaccine response can be at least partially counteracted by the use of an adjuvanted vaccine and/or a high-dose antigen or antigens.

Accordingly, the invention provides methods for enhancing an immune response to a vaccine in a subject whose immune system is compromised, e.g., immunosuppressed or at risk of developing immunosuppression. Such methods comprise administration of a vaccine composition that either (i) is adjuvanted, (ii) contains one or more high-dose antigens, to such subjects in an amount effective to enhance their immune responses to the vaccine.

Immunomodulatory Therapy

As used herein, "an immunomodulatory therapy" refers to any medical interventions, such as medications, that cause modulations in an immune response in patients. Such modulatory effects include immunosuppression, which can cause reduced immune response to a vaccine, leaving the recipient of the therapy more susceptible to an infection or related disease. Examples of immunomodulatory therapies include statins, non-steroidal anti-inflammatory drugs (NSAIDs), interferons, antipsychotics, etc.

Statins

As used herein, statins refer to a class of drugs generally known as HMG-CoA reductase inhibitors and also encompass other compounds having equivalent biological activities (i.e., the ability to inhibit HMG-CoA reductase activities). Statins referred to in the present disclosure may be non-synthetic (e.g., fermentation-derived or naturally occurring) or synthetic. Non-limiting examples of non-synthetic statins include: Pravastatin, Simvastatin, Lovastatin and Mevastatin. Non-limiting examples of synthetic statins include: Fluvastatin, Atorvastatin, Cerivastatin, Rosuvastatin and Pitavastatin. Any statins may be used in combination, either administered simultaneously or separately but in conjunction with each other. Statins may also be administered as combination formulations that include at least one statin and at least one non-statin compound. Examples of statin-containing products include, but are not limited to: ADVICOR® (niacin extended-release and lovastatin), CADUET® (amlodipine besylate/atorvastatin calcium), VYTORIN® (simvastatin and ezetimibe) and SIMCOR® (simvastatin niacin extended release).

A "statin therapy" therefore refers to a regimen that includes one or more statins either alone or in any combination, regardless of a particular condition, for which the statin or statins are being administered. In some embodiments, a statin therapy includes at least one synthetic statin.

NSAIDs

Nonsteroidal anti-inflammatory drugs, usually abbreviated to NSAIDs, are a class of drugs that provides analgesic (pain-killing) and antipyretic (fever-reducing) effects, and, in higher doses, anti-inflammatory effects. NSAIDs can be classified based on their chemical structure or mechanism of action. Typically, older NSAIDs were known long before their mechanism of action was elucidated and were for this reason classified by chemical structure or origin. Newer substances, on the other hand, are more often classified by mechanism of action.

Non-limiting examples of NSAIDs include: Salicylates (e.g., Aspirin (acetylsalicylic acid), Diflunisal (Dolobid™), Salsalate (Disalcid™) and Choline Magnesium Trisalicylate (Trilisate™)); Propionic acid derivatives (e.g., Ibuprofen, Dexibuprofen, Naproxen, Fenoprofen, Ketoprofen, Dexketoprofen, Flurbiprofen, Oxaprozin and Loxoprofen); Acetic acid derivatives (e.g., Indomethacin, Tolmetin, Sulindac, Etodolac, Ketorolac, Diclofenac, Aceclofenac and Nabumetone); Enolic acid (Oxicam) derivatives (e.g., Piroxicam, Meloxicam, Tenoxicam, Droxicam, Lornoxicam and Isoxicam); Anthranilic acid derivatives (Fenamates) (e.g., Mefenamic acid, Meclofenamic acid, Flufenamic acid and Tolfenamic acid); Selective COX-2 inhibitors (Coxibs) (e.g., Celecoxib, Rofecoxib, Valdecoxib, Parecoxib, Lumiracoxib, Etoricoxib and Firocoxib); Sulfonanilides (e.g., Nimesulide) and others, such as Licofelone, H-harpagide and Lysine clonixinate.

Interferons

Non-limiting examples of therapeutic interferons available in the market include: Interferon alpha 2a (e.g., Roferon A); Interferon alpha 2b (Intron A/Reliferon/Uniferon); Human leukocyte Interferon-alpha (HuIFN-alpha-Le) (Multiferon); Interferon beta 1a, liquid form (Rebif); Interferon beta 1a, lyophilized (Avonex); Interferon beta 1a, biogeneric (Iran) (Cinnovex); Interferon beta 1b (Betaseron/Betaferon); Interferon gamma 1b (Actimmune); PEGylated interferon alpha 2a (Pegasys); PEGylated interferon alpha 2a (Egypt) (Reiferon Retard); PEGylated interferon alpha 2b (PegIntron); and PEGylated interferon alpha 2b plus ribavirin (Canada) (Pegetron).

Antipsychotics and Antidepressants

Non-limiting examples of antipsychotics and/or antidepressants that may cause immunosuppression include: clozapine, haloperidol, as well as inhibitors of serotonin receptors and/or dopamine receptors. Additional examples include but are not limited to: SB-258719 (a neutral 5HT7R antagonist available from GSK), SB-258741 ("AFZ"; a partial inverse 5HT7R agonist available from GSK), SB-269970 (a robust 5HT7R inverse agonist available from GSK), Risperidone (an antagonist of the D1 and D2 dopamine receptors and an inverse agonist of the 5HT7 serotonin receptors; also an inverse agonist of H1 and H2 histamine receptors), Sertindole (binds to D2, 5-HT2A, 5-HT2C, 5-HT6, 5-HT7, D3, a1); Ziprasidone (binds to D2, 5-HT2A, 5-HT1A, 5-HT1D, 5-HT2C, 5-HT7, D3, a1, NRI, SRI); Loxapine (binds to D2, 5-HT2A, 5-HT6, 5-HT7, D1, D4, a1, M1, H1, NRI); Zotepine (binds to D2, 5-HT2A, 5-HT2C, 5-HT6, 5-HT7, D1, D3, D4, a1, H1, NRI); Clozapine (binds to D2, 5-HT2A, 5-HT1A, 5-HT3, 5-HT6, 5-HT7, D1, D3, D4, a1, a2, M1, H1); Olanzapine (binds to D2, 5-HT2A, 5-HT2C, 5-HT3, 5-HT6, D1, D3, D4, D5, a1, M1-5, H1), Quetiapine (binds to D2, 5-HT2A, 5-HT6, 5-HT7, a1, a2, H1); Promethazine (a strong antagonist of the H1 histamine receptor with weak to moderate affinity for the 5HT2a/c serotonin receptors and dopamine D2 receptor; also a blocker of Na+ channels). Certain ion channel blockers may be also suitable. Examples include, but are not limited to: inhibitors and blockers of voltage-dependent Na+ channels and cholinesterase, involved in lipid transport and metabolism, such as Dibucaine (a butynesterase inhibitor); inhibitors and blockers of voltage-gated L-type calcium channels (such as Nimodipine); inhibitors and blockers of sodium channels such as Aprindine (a Class 1b antiarrhythmic membrane stabilizing agent), Amiloride (a direct blocker of epithelial sodium channel ENaC); and inhibitors and blockers of delayed inward rectifier potassium channels and L-type calcium channels such as Ibutilide hemifumarate (a Class III antiarrhythmic agent)

Subjects

The terms "subject," "patient" and "individual" may be used interchangeably herein. As already alluded to, the methods and compositions described herein are useful for immunizing immunocompromised subjects or those at risk of developing immunosuppression. Described methods and compositions are particularly useful for eliciting sufficient immunoprotection in those who are immunosuppressed or at risk of developing immunosuppression due to certain medications that may render the subject vulnerable to infection.

Thus, in the context of the invention, suitable target populations include subjects on certain therapies, long-term therapies in particular. These include subjects on a statin therapy, regardless of the age of the subject, including a long-term use of statin. These also include subjects on an NSAID therapy, regardless of the age of the subject, including a long-term use of NSAID. Target populations also include subjects on more than one such therapies. For example, a subject may be on one or more statin therapies, one or more NSAID therapies, or combination of both.

When an individual's immune system is not functioning properly, the individual is generally said to be "immunocompromised." Thus, "an immunocompromised subject" is a subject with reduced ability to elicit an appropriate immune response due to any host-related, medical-related or pharmacological related factor. An immunocompromised individual may exhibit one or more types of impairment of the immune system, such as immunosuppression (e.g., weakened immunity), immunodeficiency, altered or overactive immune system, autoimmunity, or any combination thereof. Thus, an immunocompromised individual is not fully immune-competent.

In some population groups, subjects may be immunocompromised as part of normal development such as age-related conditions, not related to a specific disease or disorder. For example, very young children (e.g., infants) and the elderly may be considered not fully immune-competent. According to the invention, a target population of particular interest includes individuals who are currently on an immunomodulatory therapy (e.g., taking statin, NSAID, etc.) who have recently received an immunomodulatory therapy (e.g., taking statin, NSAID, etc.), as well as those who are about to or scheduled to start a therapy that includes an immunomodulatory therapy (e.g., taking statin, NSAID, etc.), e.g., a synthetic statin. Any of such subpopulations of patients may be collectively said to be "on immunomodulatory therapy," for example, "on statin therapy." In some embodiments, a target population comprises or consists of individuals on at least one synthetic statin.

In some embodiments, a subject has been (and continues to be) on an immunomodulatory therapy (e.g., a statin therapy, an NSAID therapy, etc.) for at least 2 days, at least 3 days, at least 4 days, at least 5 days, at least 6 days, at least 7 days, at least 10 days, at least 2 weeks, at least 3 weeks, at least 4 weeks, at least 6 weeks, at least 8 weeks, at least 12 weeks, or longer. In some embodiments, a subject was previously on an immunomodulatory therapy (e.g., a statin therapy, an NSAID therapy, etc.) as above, but has ceased such therapy within the last 6 weeks, 5 weeks, 4 weeks, 3 weeks, 2 weeks, 1 week, 6 days, 5 days, 4 days, 3 days or 2 days. In yet other embodiments, a subject has not yet been on an immunomodulatory therapy (e.g., a statin therapy, an NSAID therapy, etc.) but is scheduled to or is about to begin such a therapy within the next day, 2 days, 3 days, 4 days, 5 days, 6 days, 7 days, 10 days, 2 weeks, 3 weeks, 4 weeks, 5 weeks or 6 weeks. A long-term or chronic use of an immunomodulatory therapy (e.g., a statin therapy, an NSAID therapy, etc.) may refer to a duration of at least 4 weeks, inclusive.

In the context of the present disclosure, it shall be understood that a subject is "at risk of immunosuppression" if the subject has propensity for developing a condition that includes suppressed immune responses or if the subject meets certain criteria for a population associated with heightened risk of immunosuppression or susceptible to having a compromised immune system. The term "susceptible" means having an increased risk for and/or a propensity for (typically based on age, genetic predisposition, environmental factors, personal history, or combinations thereof) something, i.e., a disease, disorder, or condition (such as, for example, compromised immune response) than is observed in the general population. For example, a subject who is about to start on an immunomodulatory therapy (e.g., a statin therapy, an NSAID therapy, etc.) is at risk of immunosuppression and thus may benefit from the methods described herein in order to boost an immune response to a vaccine.

Subjects may be selected on the basis of certain criteria (i.e., a target population). As an example, among statin recipients, a population of individuals associated with at least one synthetic statins may be at higher risk of immunosuppression than those associated with non-synthetic statins.

Certain disease and disorders are known to be associated with impaired immunity in affected individuals. Impaired immunity may involve a suppressed immune system, an overactive immune system, autoimmunity, or any combination thereof. Immunosuppression includes, without limitation, primary immune deficiency and secondary or acquired immune deficiency. Primary immune deficiency may be caused by genetic abnormality. Secondary or acquired immune deficiency is commonly associated with certain disease, such as AIDS, as well as temporary acquired immune deficiencies due to certain drugs, such as statins NSAIDs, chemotherapeutics or immunosuppressing agents administered following organ transplants. One's immune system can also be weakened by certain living conditions or environmental factors, including smoking, alcohol consumption and poor nutrition.

For example, a target population may consist of subjects of one age group, such as infants and elderly subjects. As used herein, an "elderly subject" is a human individual of age 65 or older. An "infant," is a human individual between the age of 0-12 months (0 being a newborn), for example, between 0-3 months, between 0-6 months, between 0-9 months, and between 6-12 months. In some embodiments, a target population may consist of human subjects between the age of 18 and 65, between the age of 18 and 60, between the age of 18 and 55, between the age of 18 and 50, between the age of 18 and 45, between the age of 45 and 65, between the age of 45 and 60, between the age of 18 and 24, between the age of 18 and 35, etc. In any one of such target population, the subjects may be further associated with at least one risk factors, including, without limitation: chronic or genetic disease or disorder and medication/therapeutics.

In some embodiments, a suitable subject is a non-elderly subject, e.g., a human individual under the age of 65. In another embodiment, the subject is below 65, but 18 years or older. Such subjects may be on an immunomodulatory therapy (e.g., a statin therapy, an NSAID therapy, etc.), for example, a statin therapy incorporating at least one synthetic statin.

As used herein, "enhancing an immune response" may involve, for example, improving or augmenting immunogenicity, as measured by any suitable methods known or accepted in the art. An "enhanced immune response" is achieved when a statistically significant augmentation of immune responses in one measurement or combination of measurements is observed among a population of subjects meeting certain criteria, i.e., a target population. A target population may consist of individuals who are on an immunomodulatory therapy (e.g., a statin therapy, an NSAID therapy, etc.). In some embodiments, a subset of such population may represent a particular category of individuals, such as age groups. The phrase "boosting an immune response" may refer to enhancement of a previously primed immune response in a subject.

The Adjuvant

An "adjuvanted vaccine" comprises one or more adjuvants. Accordingly, in some embodiments, compositions of the invention comprise an adjuvant, which can function to enhance the immune responses (humoral and/or cellular) elicited in a patient who receives the composition. Useful adjuvants include, but are not limited to: aluminum salt-based adjuvants (e.g., aluminum phosphate and aluminum hydroxide), agonists of Toll-like receptors (e.g., human TLR1 agonists, human TLR2 agonists, human TLR3 agonists, human TLR4 agonists, human TLR5 agonists, human TLR6 agonists, human TLR7 agonists, human TLR8 agonists, human TLR9 agonists, and human TLR10 agonists), emulsion-based adjuvants, and virus-like particle-based adjuvants, such as virosomes.

In some embodiments, vaccine adjuvants for use with the invention comprise an oil-in-water emulsion.

Oil-in-water emulsions have been found to be particularly suitable for use in adjuvanting vaccines, including viral vaccines, such as influenza virus vaccines. Various such emulsions are known, and they typically include at least one oil and at least one surfactant, with the oil(s) and surfactant(s) being biodegradable (metabolisable) and biocompatible. The oil droplets in the emulsion are generally less than 5 μm in diameter, and ideally the majority of oil droplets in the emulsion have a sub-micron diameter (e.g., at least 90% by number of the oil droplets have a sub-micron diameter), with these small sizes being achieved with a microfluidiser to provide stable emulsions. Droplets with a size less than 220 nm (e.g., less than 220 nm, less than 200 nm, less than 190 nm, less than 180 nm, less than 170 nm, less than 160 nm, less than 150 nm, less than 140 nm, less than 130 nm, less than 120 nm, less than 110 nm, less than 100 nm, etc.) are preferred as they can be subjected to filter sterilization. For example, suitable oil-in-water emulsions include those with average oil droplet sizes ranging between about 100-200 nm, about 110-200 nm, about 120-200 nm, about 130-200 nm, about 140-200 nm, about 100-190 nm, 100-180 nm, 100-170 nm, 100-160 nm, 100-150 nm, 130-190 nm, 135-185 nm, 140-180 nm, 145-175 nm, or 150-170 nm.

The emulsion can comprise oils such as those from an animal (such as fish) or vegetable source. Sources for vegetable oils include nuts, seeds and grains. Peanut oil, soybean oil, coconut oil, and olive oil, the most commonly available, exemplify the nut oils. Jojoba oil can be used, e.g., obtained from the jojoba bean. Seed oils include safflower oil, cottonseed oil, sunflower seed oil, sesame seed oil and the like. In the grain group, com oil is the most readily available, but the oil of other cereal grains such as wheat, oats, rye, rice, teff, triticale and the like may also be used. 6-10 carbon fatty acid esters of glycerol and 1,2-propanediol, while not occurring naturally in seed oils, may be prepared by hydrolysis, separation and esterification of the appropriate materials starting from the nut and seed oils. Fats and oils from mammalian milk are metabolizable and may therefore be used in the practice of this invention. The procedures for separation, purification, saponification and other means necessary for obtaining pure oils from animal sources are well known in the art. Most fish contain metabolizable oils which may be readily recovered. For example, cod liver oil, shark liver oils, and whale oil such as spermaceti exemplify several of the fish oils which may be used herein. A number of branched chain oils are synthesized biochemically in 5-carbon isoprene units and are generally referred to as terpenoids. Shark liver oil contains a branched, unsaturated terpenoids known as squalene, 2,6,10,15,19,23-hexamethyl-2,6,10,14,18,22-tetracosahexaene, which is particularly preferred herein. Squalane, the saturated analog to squalene, is also a preferred oil. Fish oils, including squalene and squalane, are readily available from commercial sources or may be obtained by methods known in the art. Other preferred oils are the tocopherols (see below). Mixtures of oils can be used.

Surfactants can be classified by their 'HLB' (hydrophile/lipophile balance). Preferred surfactants of the invention have a HLB of at least 10, preferably at least 15, and more preferably at least 16. The invention can be used with surfactants including, but not limited to: the polyoxyethylene sorbitan esters surfactants (commonly referred to as the Tweens), especially polysorbate 20 and polysorbate 80; copolymers of ethylene oxide (EO), propylene oxide (PO), and/or butylene oxide (BO), sold under the DOWFAX™ tradename, such as linear EO/PO block copolymers; octoxynols, which can vary in the number of repeating ethoxy (oxy-1,2-ethanediyl) groups, with octoxynol-9 (Triton X-100, or t-octylphenoxypolyethoxyethanol) being of particular interest; (octylphenoxy)polyethoxyethanol (IGEPAL CA-630/NP-40); phospholipids such as phosphatidylcholine (lecithin); nonylphenol ethoxylates, such as the Tergitol™ NP series; polyoxyethylene fatty ethers derived from lauryl, cetyl, stearyl and oleyl alcohols (known as Brij surfactants), such as triethyleneglycol monolauryl ether (Brij 30); and sorbitan esters (commonly known as the SPANs), such as sorbitan trioleate (Span 85) and sorbitan monolaurate. Nonionic surfactants are preferred. Preferred surfactants for including in the emulsion are Tween 80 (polyoxyethylene sorbitan monooleate or polysorbate 80), Span 85 (sorbitan trioleate), lecithin and Triton X-100.

Mixtures of surfactants can be used, e.g., Tween 80/Span 85 mixtures. A combination of a polyoxyethylene sorbitan ester such as polyoxyethylene sorbitan monooleate (polysorbate 80) and an octoxynol such as t-octylphenoxypolyethoxyethanol (Triton X-100) is also suitable. Another useful combination comprises laureth 9 plus a polyoxyethylene sorbitan ester and/or an octoxynol.

Preferred amounts of surfactants (% by weight) are: polyoxyethylene sorbitan esters (such as polysorbate 80) 0.01 to 1%, in particular about 0.1%; octyl- or nonylphenoxy polyoxyethanols (such as Triton X-100, or other detergents in the Triton series) 0.001 to 0.1%, in particular 0.005 to 0.02%; polyoxyethylene ethers (such as laureth 9) 0.1 to 20%, preferably 0.1 to 10% and in particular 0.1 to 1% or about 0.5%.

Preferred emulsion adjuvants have an average droplets size of <1μm, e.g., <750 nm, <500 nm, <400 nm, <300 nm, <250 nm, <220 nm, <200 nm, <190 nm, <180 nm, <170 nm, <160 nm, <150 nm, or smaller. These droplet sizes can conveniently be achieved by techniques such as microfluidization and suitable filtration (see, for example, International Patent Publications: WO 2011/067669, WO 2011/067673 and WO 2011/067672, the contents of which are incorporated herein).

Provided below are examples of specific oil-in-water emulsion adjuvants useful for the invention:

A submicron emulsion of squalene, polysorbate 80, and sorbitan trioleate. These three components can be present at a volume ratio of 10:1:1 or a weight ratio of 39:47:47. The composition of the emulsion by volume can be about 5% squalene, about 0.5% polysorbate 80 and about 0.5% sorbitan trioleate. In weight terms, these ratios become 4.3%> squalene, 0.5%> polysorbate 80 and 0.48%> sorbitan trioleate. This adjuvant is known as "MF59," as previously described. The MF59 emulsion may advantageously include a buffer, such as citrate ions, e.g., 10 mM sodium citrate buffer.

An emulsion of squalene, a tocopherol, and polysorbate 80. The emulsion may include phosphate buffered saline. It may also include Span 85 (e.g., at 1%>) and/or lecithin. These emulsions may have from 2 to 10%> squalene, from 2 to 10%> tocopherol and from 0.3 to 3%> polysorbate 80, and the weight ratio of squalene: tocopherol is preferably <1 as this provides a more stable emulsion. Squalene and polysorbate 80 may be present volume ratio of about 5:2 or at a weight ratio of about 11:5. Thus the three components (squalene, tocopherol, polysorbate 80) may be present at a weight ratio of 1068:1186:485 or around 55:61:25. One such emulsion ("AS03") can be made by dissolving Tween 80 in PBS to give a 2%> solution, then mixing 90 ml of this solution with a mixture of (5 g of DL-a-tocopherol and 5 ml squalene), then microfluidising the mixture. The resulting emulsion may have submicron oil droplets e.g., with an average diameter of between 100 and 250 nm, preferably about 180 nm. The emulsion may also include a 3-de-O-acylated monophosphoryl lipid A (3d-MPL). Another useful emulsion of this type may comprise, per human dose, 0.5-10 mg squalene, 0.5-11 mg tocopherol, and 0.1-4 mg polysorbate 80, e.g., in the ratios discussed above.

An emulsion of squalene, a tocopherol, and a Triton detergent (e.g. Triton X-100). The emulsion may also include a 3d-MPL (see below). It may contain a buffer, such as a phosphate buffer.

An emulsion comprising a polysorbate (e.g., polysorbate 80), a Triton detergent (e.g., Triton X-100) and a tocopherol (e.g. an a-tocopherol succinate). The emulsion may include these three components at a mass ratio of about 75:11:10 (e.g. 750 µg/ml polysorbate 80, 110 µg/ml Triton X-100 and 100 µg/ml a-tocopherol succinate), and these concentrations should include any contribution of these components from antigens. The emulsion may also include squalene. The emulsion may also include a 3d-MPL (see below). The aqueous phase may contain a buffer, such as a phosphate buffer.

An emulsion of squalane, polysorbate 80 and poloxamer 401 ("Pluronic™ L121"). The emulsion can be formulated in phosphate buffered saline, pH 7.4. This emulsion is a useful delivery vehicle for muramyl dipeptides, and has been used with threonyl-MDP in the "SAF-1" adjuvant (0.05-1% Thr-MDP, 5% squalane, 2.5% Pluronic L121 and 0.2% polysorbate 80). It can also be used without the Thr-MDP, as in the "AF" adjuvant (5% squalane, 1.25% Pluronic L121 and 0.2%> polysorbate 80). Micro fluidisation is preferred.

An emulsion comprising squalene, an aqueous solvent, a polyoxyethylene alkyl ether hydrophilic nonionic surfactant (e.g. polyoxyethylene (12) cetostearyl ether) and a hydrophobic nonionic surfactant (e.g. a sorbitan ester or mannide ester, such as sorbitan monoleate or 'Span 80'). The emulsion is preferably thermoreversible and/or has at least 90% of the oil droplets (by volume) with a size less than 200 nm. The emulsion may also include one or more of: alditol; a cryoprotective agent (e.g. a sugar, such as dodecylmaltoside and/or sucrose); and/or an alkylpolyglycoside. The emulsion may include a TLR4 agonist. Such emulsions may be lyophilized.

An emulsion of squalene, poloxamer 105 and Abil-Care. The final concentration (weight) of these components in adjuvanted vaccines are 5% squalene, 4% poloxamer 105 (pluronic polyol) and 2% Abil-Care 85 (Bis-PEG/PPG-16/16 PEG/PPG-16/16 dimethicone; caprylic/capric triglyceride).

An emulsion having from 0.5-50% of an oil, 0.1-10% of a phospholipid, and 0.05-5% of a non-ionic surfactant. Preferred phospholipid components are phosphatidyl-choline, phosphatidylethanolamine, phosphatidylserine, phosphatidylinositol, phosphatidylglycerol, phosphatidic acid, sphingomyelin and cardiolipin. Submicron droplet sizes are advantageous.

A submicron oil-in-water emulsion of a non-metabolisable oil (such as light mineral oil) and at least one surfactant (such as lecithin, Tween 80 or Span 80). Additives may be included, such as QuilA saponin, cholesterol, a saponin-lipophile conjugate (such as GPI-0100, produced by addition of aliphatic amine to desacylsaponin via the carboxyl group of glucuronic acid), dimethyidioctadecylammonium bromide and/or N,N-dioctadecyl-N,N-bis (2-hydroxyethyl)propanediamine.

An emulsion in which a saponin (e.g., QuilA and QS21) and a sterol (e.g., cholesterol) are associated as helical micelles.

An emulsion comprising a mineral oil, a non-ionic lipophilic ethoxylated fatty alcohol, and a non-ionic hydrophilic surfactant (e.g., an ethoxylated fatty alcohol and/or polyoxyethylene-polyoxypropylene block copolymer).

An emulsion comprising a mineral oil, a non-ionic hydrophilic ethoxylated fatty alcohol, and a non-ionic lipophilic surfactant (e.g., an ethoxylated fatty alcohol and/or polyoxyethylene-polyoxypropylene block copolymer).

In some embodiments an emulsion may be mixed with antigen extemporaneously, at the time of delivery, and thus the adjuvant and antigen may be kept separately in a packaged or distributed vaccine, ready for final formulation at the time of use. In other embodiments an emulsion is mixed with antigen during manufacture, and thus the composition is packaged in a liquid adjuvanted form, as in the FLUAD™ product. The antigen will generally be in an aqueous form, such that the vaccine is finally prepared by mixing two liquids. The volume ratio of the two liquids for mixing can vary (e.g., between 5:1 and 1:5) but is generally about 1:1. Where concentrations of components are given in the above descriptions of specific emulsions, these concentrations are typically for an undiluted composition, and the concentration after mixing with an antigen solution will thus decrease.

After the antigen and adjuvant have been mixed, haemagglutinin antigen will generally remain in aqueous solution but may distribute itself around the oil/water interface. In general, little if any haemagglutinin will enter the oil phase of the emulsion.

Where a composition includes a tocopherol, any of the α, β, γ, δ, ε or ξ tocopherols can be used (alone or in combination), but α-tocopherols are preferred. The tocopherol can take several forms, e.g., different salts and/or isomers. Salts include organic salts, such as succinate, acetate, nicotinate, etc. D-a-tocopherol and DL-a-tocopherol can both be used. Tocopherols are advantageously included in vaccines for use in elderly patients (e.g., aged 60 years or older or 65 years or older) because vitamin E has been reported to have a positive effect on the immune response in this patient group. They also have antioxidant properties that may help to stabilize the emulsions. A preferred a-tocopherol is DL-a-tocopherol, and the preferred salt of this tocopherol is the succinate. The succinate salt has been found to cooperate with TNF-related ligands in vivo. Moreover, a-tocopherol succinate is known to be compatible with influenza vaccines and to be a useful preservative as an alternative to mercurial compounds.

High-Dose Vaccines

In the context of the present disclosure, a high-dose vaccine refers to a vaccine containing an antigen (i.e., immunogen) that is at least about a twofold the amount of the same antigen contained in a standard dose vaccine, for example, two-fold, three-fold, four-fold, five-fold, six-fold, seven-fold, eight-fold, nine-fold, and ten-fold, which may be alternatively expressed as 2x, 3x, 4x, 5x, 6x, 7x, 8x, 9x, and 10x, respectively. Standard dose vaccines are those typically commercially available, which are not specifically labeled or marketed as high-dose or low-dose. In the case of influenza vaccines, a standard dose is about 15 µg of antigen per strain (see below for more detail).

The Influenza Virus Antigen

The invention uses an influenza virus antigen, typically comprising hemagglutinin, to immunize a subject. The antigen will typically be prepared from influenza virions but, as an alternative, antigens such as haemagglutinin can be expressed in a recombinant host (e.g., in an insect cell line using a baculovirus vector) and used in purified form. In general, however, antigens may be from virions.

The antigen may take the form of a live virus or, more preferably, an inactivated virus. Chemical means for inactivating a virus include treatment with an effective amount of one or more of the following agents: detergents, formaldehyde, formalin, β-propiolactone, or UV light. Additional chemical means for inactivation include treatment with methylene blue, psoralen, carboxyfullerene (C60) or a combination of any thereof. Other methods of viral inactivation are known in the art, such as for example binary ethylamine, acetyl ethyleneimine, or gamma irradiation. The INFLEXAL™ product is a whole virion inactivated vaccine.

Where an inactivated virus is used, the vaccine may comprise whole virion, split virion, or purified surface antigens (including hemagglutinin and, usually, also including neuraminidase).

An inactivated but non-whole cell vaccine (e.g., a split virus vaccine or a purified surface antigen vaccine) may include matrix protein, in order to benefit from the additional T cell epitopes that are located within this antigen. Thus, a non-whole cell vaccine (particularly a split vaccine) that includes haemagglutinin and neuraminidase may additionally include MI and/or M2 matrix protein. Nucleoprotein may also be present.

Virions can be harvested from virus-containing fluids by various methods. For example, a purification process may involve zonal centrifugation using a linear sucrose gradient solution that includes detergent to disrupt the virions. Antigens may then be purified, after optional dilution, by diafiltration.

Split virions are obtained by treating purified virions with detergents and/or solvents to produce subvirion preparations, including the 'Tween-ether' splitting process. Methods of splitting influenza viruses are well known in the art. Splitting of the virus is typically carried out by disrupting or fragmenting whole virus, whether infectious or non-infectious with a disrupting concentration of a splitting agent. The disruption results in a full or partial solubilisation of the virus proteins, altering the integrity of the virus. Preferred splitting agents are non-ionic and ionic (e.g. cationic) surfactants. Suitable splitting agents include, but are not limited to: ethyl ether, polysorbate 80, deoxycholate, tri-N-butyl phosphate, alkylglycosides, alkylthioglycosides, acyl sugars, sulphobetaines, betaines, polyoxyethylenealkylethers, N,N-dialkyl-Glucamides, Hecameg, alkylphenoxy-polyethoxyethanols, quaternary ammonium compounds, sarcosyl, CTABs (cetyl trimethyl ammonium bromides), tri-N-butyl phosphate, Cetavlon, myristyltrimethylammonium salts, lipofectin, lipofectamine, and DOT-MA, the octyl- or nonylphenoxy polyoxyethanols (e.g. the Triton surfactants, such as Triton X-100 or Triton N101), nonoxynol 9 (NP9) Sympatens-NP/090,) polyoxyethylene sorbitan esters (the Tween surfactants), polyoxyethylene ethers, polyoxyethlene esters, etc. One useful splitting procedure uses the consecutive effects of sodium deoxycholate and formaldehyde, and splitting can take place during initial virion purification (e.g. in a sucrose density gradient solution). Thus a splitting process can involve clarification of the virion-containing material (to remove non-virion material), concentration of the harvested virions (e.g. using an adsorption method, such as CaHP04 adsorption), separation of whole virions from non-virion material, splitting of virions using a splitting agent in a density gradient centrifugation step (e.g. using a sucrose gradient that contains a splitting agent such as sodium deoxycholate), and then filtration (e.g. ultrafiltration) to remove undesired materials. Split virions can usefully be resuspended in sodium phosphate-buffered isotonic sodium chloride solution. The BEGRIVAC™, FLUARIX™, FLUZONE™ and FLUSHIELD™ products are split vaccines.

Purified surface antigen vaccines comprise the influenza surface antigens haemagglutinin and, typically, also neuraminidase. Processes for preparing these proteins in purified form are well known in the art. The FLUVIRIN™, AGRIPPAL™ and INFLUVAC™ products are subunit vaccines.

Another form of inactivated influenza antigen is the virosome (nucleic acid free viral-like liposomal particles). Virosomes can be prepared by solubilization of influenza virus with a detergent followed by removal of the nucleocapsid and reconstitution of the membrane containing the viral glycoproteins. An alternative method for preparing virosomes involves adding viral membrane glycoproteins to excess amounts of phospholipids, to give liposomes with viral proteins in their membrane. The invention can be used to store bulk virosomes, as in the INFLEXAL V™ product. In some embodiments, the influenza antigen is not in the form of a virosome.

The influenza virus may be attenuated. The influenza virus may be temperature-sensitive. The influenza virus may be cold-adapted. These three features are particularly useful when using live virus as a vaccine antigen.

With respect to inactivated influenza vaccines currently available, HA is the main immunogen, and vaccine doses are standardized by reference to HA levels, typically measured by SRID. Existing vaccines typically contain about 15 μg of HA per strain, although lower doses can be used, e.g., for children, or in pandemic situations, or when used in conjunction with an adjuvant. Fractional doses such as ½ (e.g., 7.5 μg HA per strain), ¼ and ⅛ have been used, as have higher doses (e.g., 2×, 3× or 9× doses).

Thus, vaccines of the present invention may include between about 0.1 and about 150 μg of an antigen. For example, HA per influenza strain, preferably between 0.1 and 50 μg, e.g., 0.1-20 μg, 0.1-15 μg, 0.1-10 μg, 0.1-7 μg, 0.5-5 μg, etc. Particular doses include, e.g., about 45 μg, about 30 μg, about 15 μg; about 10 μg, about 7.5 μg, about 5 μg, about 3.8 μg, about 1.9 μg, about 1.5 μg, etc. per strain.

For live vaccines, dosing is measured by median tissue culture infectious dose (TCID50) rather than HA content, and a TCID50 of between $10^6$ and $10^8$ (preferably between $10^{6.5}$-$10^{7.5}$) per strain is typical.

As used herein, a "high-dose influenza vaccine" may contain between about 30 μg and 150 μg of an antigen (e.g., HA) per strain, as opposed to the standard-dose vaccine, which typically contains 15 μg of an antigen (e.g., HA) per strain. Thus, in some embodiments, a high-dose vaccine contains about 30 μg, about 35 μg, about 40 μg, about 45 μg, about 50 μg, about 55 μg, about 60 μg, about 65 μg, about 70 μg, about 75 μg, about 80 μg, about 85 μg, about 90 μg about 100 μg about 110 μg about 120 μg about 130 μg about 140 μg about 150 μg of antigen per strain.

A "low-dose influenza vaccine," on the other hand, refers to a vaccine composition that contains less than 15 μg of an antigen (e.g., HA) per strain, for example, about 12.5 μg, about 10 μg, about 7.5 μg, about 5 μg, about 4 μg, about 3 μg, about 2.5 μg. In some embodiments, any of high-dose vaccines, standard-dose vaccines, and low-dose vaccines may be adjuvanted.

Influenza virus strains for use in vaccines change from season to season. In the current inter-pandemic, period, vaccines typically include two influenza A strains (H1N1 and H3N2) and one or two influenza B strain, and trivalent or tetravalent vaccines are typical for use with the invention. Compositions of the invention comprise antigen from influenza B virus and optionally comprise antigen from at least one influenza A virus. Where the composition of the invention comprises antigen from influenza A virus(es), the invention may use seasonal and/or pandemic strains. Depending on the season and on the nature of the antigen included in the vaccine, the invention may include (and protect against) one or more of influenza A virus hemagglutinin subtypes HI, H2, H3, H4, H5, H6, H7, H8, H9, H10, HI 1, H12, H13, H14, H15 or H16. The vaccine may additionally include neuraminidase from any of NA subtypes NI, N2, N3, N4, N5, N6, N7, N8 or N9.

The invention can thus be used with pandemic influenza A virus strains. Characteristics of a pandemic strain are: (a) it contains a new hemagglutinin compared to the hemagglutinins in currently-circulating human strains, i.e., one that has not been evident in the human population for over a decade (e.g., H2), or has not previously been seen at all in the human population (e.g., H5, H6 or H9, that have generally been found only in bird populations), such that the vaccine recipient and the general human population are immunologically naive to the strain's hemagglutinin; (b) it is capable of being transmitted horizontally in the human population; and (c) it is pathogenic to humans. Pandemic strains include, but are not limited to, H2, H5, H7 or H9 subtype strains, e.g., H5N1, H5N3, H9N2, H2N2, H7N1 and H7N7 strains. Within the H5 subtype, a virus may fall into a number of clades e.g. clade 1 or clade 2. Six sub-clades of clade 2 have been identified with sub-clades 1, 2 and 3 having a distinct geographic distribution and are particularly relevant due to their implication in human infections.

Influenza B virus currently does not display different HA subtypes, but influenza B virus strains do fall into two distinct lineages. These lineages emerged in the late 1980s and have HAs which can be antigenically and/or genetically distinguished from each other. Current influenza B virus strains are either B/Victoria/2/87-like or B/Yamagata/16/88-like. These strains are usually distinguished antigenically, but differences in amino acid sequences have also been described for distinguishing the two lineages, e.g., B/Yamagata/16/88-like strains often (but not always) have HA proteins with deletions at amino acid residue 164, numbered relative to the 'Lee40' HA sequence. The invention can be used with antigens from a B virus of either lineage, or with antigens from both lineages.

Where a vaccine includes more than one strain of influenza, the different strains are typically grown separately and are mixed after the viruses have been harvested and antigens have been prepared. Thus a manufacturing process of the invention may include the step of mixing antigens from more than one influenza strain.

An influenza virus used with the invention may be a reassortant strain, and may have been obtained by reverse genetics techniques. Reverse genetics techniques allow influenza viruses with desired genome segments to be prepared in vitro using plasmids. Typically, it involves expressing (a) DNA molecules that encode desired viral RNA molecules e.g. from polI promoters or bacteriophage RNA polymerase promoters, and (b) DNA molecules that encode viral proteins, e.g., from polII promoters, such that expression of both types of DNA in a cell leads to assembly of a complete intact infectious virion. The DNA preferably provides all of the viral RNA and proteins, but it is also possible to use a helper virus to provide some of the RNA and proteins. Plasmid-based methods using separate plasmids for producing each viral RNA can be used, and these methods will also involve the use of plasmids to express all or some (e.g., just the PB 1, PB2, PA and NP proteins) of the viral proteins, with up to 12 plasmids being used in some methods. To reduce the number of plasmids needed, a recent approach combines a plurality of RNA polymerase I transcription cassettes (for viral RNA synthesis) on the same plasmid (e.g., sequences encoding 1, 2, 3, 4, 5, 6, 7 or all 8 influenza A vRNA segments), and a plurality of protein-coding regions with RNA polymerase II promoters on another plasmid (e.g., sequences encoding 1, 2, 3, 4, 5, 6, 7 or all 8 influenza A mRNA transcripts). In some embodiments of the invention, methods involve: (a) PB 1, PB2 and PA mRNA-encoding regions on a single plasmid; and (b) all 8 vRNA-encoding segments on a single plasmid. Including the NA and HA segments on one plasmid and the six other segments on another plasmid can also facilitate matters.

As an alternative to using poll promoters to encode the viral RNA segments, it is possible to use bacteriophage polymerase promoters. For instance, promoters for the SP6, T3 or T7 polymerases can conveniently be used. Because of the species-specificity of poll promoters, bacteriophage polymerase promoters can be more convenient for many cell types (e.g. MDCK), although a cell must also be transfected with a plasmid encoding the exogenous polymerase enzyme.

In other techniques it is possible to use dual polI and polII promoters to simultaneously code for the viral RNAs and for expressible mRNAs from a single template.

Thus an influenza A virus may include one or more RNA segments from an A/PR/8/34 virus (typically 6 segments from A/PR/8/34, with the HA and N segments being from a vaccine strain, i.e. a 6:2 reassortant). It may also include one or more RNA segments from an A/WSN/33 virus, or from any other virus strain useful for generating reassortant viruses for vaccine preparation. An influenza A virus may include fewer than 6 (e.g., 0, 1, 2, 3, 4 or 5) viral segments from an AA/6/60 influenza virus (A/Ann Arbor/6/60). An influenza B virus may include fewer than 6 (e.g., 0, 1, 2, 3, 4 or 5) viral segments from an AA/1/66 influenza virus (B/Ann Arbor/1/66). Typically, the invention protects against a strain that is capable of human-to-human transmission, and so the strain's genome will usually include at least one RNA segment that originated in a mammalian (e.g., in a human) influenza virus. It may include NS segment that originated in an avian influenza virus.

Strains whose antigens can be included in the compositions may be resistant to antiviral therapy (e.g., resistant to oseltamivir and/or zanamivir), including resistant pandemic strains.

HA used with the invention may be a natural HA as found in a virus, or may have been modified. For instance, it is known to modify HA to remove determinants (e.g., hyperbasic regions around the cleavage site between HA1 and HA2) that cause a virus to be highly pathogenic in avian species, as these determinants can otherwise prevent a virus from being grown in eggs.

The viruses used as the source of the antigens can be grown either on eggs (e.g., specific pathogen free eggs) or on cell culture. The current standard method for influenza virus growth uses embryonated hen eggs, with virus being purified from the egg contents (allantoic fluid). More recently, however, viruses have been grown in animal cell culture and, for reasons of speed and patient allergies, this growth method is preferred.

The cell line will typically be of mammalian origin. Suitable mammalian cells of origin include, but are not limited to, hamster, cattle, primate (including humans and monkeys) and dog cells, although the use of primate cells is not preferred. Various cell types may be used, such as kidney cells, fibroblasts, retinal cells, lung cells, etc. Examples of suitable hamster cells are the cell lines having the names BHK21 or HKCC. Suitable monkey cells are e.g. African green monkey cells, such as kidney cells as in the Vero cell line. Suitable dog cells are, e.g., kidney cells, as in the CLDK and MDCK cell lines.

Thus suitable cell lines include, but are not limited to: MDCK; CHO; CLDK; HKCC; 293T; BHK; Vero; MRC-5; PER.C6; FRhL2; WI-38; etc. Suitable cell lines are widely available, e.g., from the American Type Cell Culture (ATCC) collection, from the Coriell Cell Repositories, or from the European Collection of Cell Cultures (ECACC). For example, the ATCC supplies various different Vero cells under catalog numbers CCL-81, CCL-81.2, CRL-1586 and CRL-1587, and it supplies MDCK cells under catalog number CCL-34. PER.C6 is available from the ECACC under deposit number 96022940.

The most preferred cell lines are those with mammalian-type glycosylation. As a less-preferred alternative to mammalian cell lines, virus can be grown on avian cell lines, including cell lines derived from ducks (e.g. duck retina) or hens. Examples of avian cell lines include avian embryonic stem cells and duck retina cells. Suitable avian embryonic stem cells include the EBx cell line derived from chicken embryonic stem cells, EB45, EB14, and EB 14-074. Chicken embryo fibroblasts (CEF) may also be used. Rather than using avian cells, however, the use of mammalian cells means that vaccines can be free from avian DNA and egg proteins (such as ovalbumin and ovomucoid), thereby reducing allergenicity.

The most preferred cell lines for growing influenza viruses are MDCK cell lines, derived from Madin Darby canine kidney. The original MDCK cell line is available from the ATCC as CCL-34, but derivatives of this cell line may also be used. For instance, a MDCK cell line has been adapted for growth in suspension culture ('MDCK 33016', deposited as DSM ACC 2219). Similarly, a MDCK-derived cell line has been developed which grows in suspension in serum-free culture ('B-702', deposited as FERM BP-7449). Non-tumorigenic MDCK cells have been described, including 'MDCK-S' (ATCC PTA-6500), 'MDCK-SF101' (ATCC PTA-6501), 'MDCK-SF102' (ATCC PTA-6502) and 'MDCK-SF103' (PTA-6503). MDCK cell lines with high susceptibility to infection have been developed, including 'MDCK.5F1' cells (ATCC CRL-12042). Any of these MDCK cell lines can be used.

Virus may be grown on cells in adherent culture or in suspension. Microcarrier cultures can also be used. In some embodiments, the cells may thus be adapted for growth in suspension.

Cell lines are preferably grown in serum-free culture media and/or protein free media. A medium is referred to as a serum-free medium in the context of the present invention in which there are no additives from serum of human or animal origin. The cells growing in such cultures naturally contain proteins themselves, but a protein-free medium is understood to mean one in which multiplication of the cells occurs with exclusion of proteins, growth factors, other protein additives and non-serum proteins, but can optionally include proteins such as trypsin or other proteases that may be necessary for viral growth.

Cell lines supporting influenza virus replication are preferably grown below 37° C. (e.g., 30-36° C., or at about 30° C., 31° C., 32° C., 33° C., 34° C., 35° C., 36° C.) during viral replication.

Methods for propagating influenza virus in cultured cells generally includes the steps of inoculating a culture of cells with an inoculum of the strain to be grown, cultivating the infected cells for a desired time period for virus propagation, such as for example as determined by virus titer or antigen expression (e.g., between 24 and 168 hours after inoculation) and collecting the propagated virus. The cultured cells are inoculated with a virus (measured by PFU or TCID50) to cell ratio of 1:500 to 1:1, preferably 1:100 to 1:5, more preferably 1:50 to 1:10. The virus is added to a suspension of the cells or is applied to a monolayer of the cells, and the virus is absorbed on the cells for at least 60 minutes but usually less than 300 minutes, preferably between 90 and 240 minutes at 25° C. to 40° C., preferably 28° C. to 37° C. The infected cell culture (e.g., monolayers) may be removed either by freeze-thawing or by enzymatic action to increase the viral content of the harvested culture supernatants. The harvested fluids are then either inactivated or stored frozen. Cultured cells may be infected at a multiplicity of infection ("m.o.i.") of about 0.0001 to 10, preferably 0.002 to 5, more preferably to 0.001 to 2. Still more preferably, the cells are infected at an m.o.i of about 0.01. Infected cells may be harvested 30 to 60 hours post infection. Preferably, the cells are harvested 34 to 48 hours post infection. Still more preferably, the cells are harvested 38 to 40 hours post infection. Proteases (typically trypsin) are generally added during cell culture to allow viral release, and the proteases can be added at any suitable stage during the culture e.g. before inoculation, at the same time as inoculation, or after inoculation.

In preferred embodiments, particularly with MDCK cells, a cell line is not passaged from the master working cell bank beyond 40 population-doubling levels.

The viral inoculum and the viral culture are preferably free from (i.e., will have been tested for and given a negative result for contamination by) herpes simplex virus, respiratory syncytial virus, parainfluenza virus 3, SARS coronavirus, adenovirus, rhinovirus, reoviruses, polyomaviruses, birnaviruses, circoviruses, and/or parvoviruses. Absence of herpes simplex viruses is particularly preferred.

Where virus has been grown on a cell line then it is standard practice to minimize the amount of residual cell line DNA in the final vaccine, in order to minimize any oncogenic activity of the DNA.

Thus a vaccine composition prepared according to the invention preferably contains less than 10 ng (preferably less than I ng, and more preferably less than 100 pg) of residual host cell DNA per dose, although trace amounts of host cell DNA may be present.

Vaccines containing <10 ng (e.g. <I ng, <100 pg) host cell DNA per 15 μg of haemagglutinin are preferred, as are vaccines containing <10 ng (e.g. <I ng, <100 pg) host cell DNA per 0.25 ml volume.

Vaccines containing <10 ng (e.g. <I ng, <100 pg) host cell DNA per 5 μg of haemagglutinin are more preferred, as are vaccines containing <10 ng (e.g. <I ng, <100 pg) host cell DNA per 0.5 ml volume.

It is preferred that the average length of any residual host cell DNA is less than 500 bp, e.g., less than 400 bp, less than 300 bp, less than 200 bp, less than 100 bp, etc.

Contaminating DNA can be removed during vaccine preparation using standard purification procedures e.g. chromatography, etc. Removal of residual host cell DNA can be enhanced by nuclease treatment e.g. by using a DNase. A convenient method for reducing host cell DNA contamination has been described in the literature, involving a two-step treatment, first using a DNase (e.g. Benzonase), which may be used during viral growth, and then a cationic detergent (e.g. CTAB), which may be used during virion disruption. Removal by β-propiolactone treatment can also be used.

Measurement of residual host cell DNA is now a routine regulatory requirement for biologicals and is within the normal capabilities of the skilled person. The assay used to measure DNA will typically be a validated assay. The performance characteristics of a validated assay can be described in mathematical and quantifiable terms, and its possible sources of error will have been identified. The assay will generally have been tested for characteristics such as accuracy, precision, specificity. Once an assay has been calibrated (e.g. against known standard quantities of host cell DNA) and tested then quantitative DNA measurements can be routinely performed. Three main techniques for DNA quantification can be used: hybridization methods, such as Southern blots or slot blots; immunoassay methods, such as the Threshold™ System; and quantitative PCR. These methods are all familiar to the skilled person, although the precise characteristics of each method may depend on the host cell in question e.g. the choice of probes for hybridization, the choice of primers and/or probes for amplification, etc. The Threshold™ system from Molecular Devices is a quantitative assay for picogram levels of total DNA, and has been used for monitoring levels of contaminating DNA in biopharmaceuticals. A typical assay involves non-sequence-specific formation of a reaction complex between a biotinylated ssDNA binding protein, a urease-conjugated anti-ssDNA antibody, and DNA. All assay components are included in the complete Total DNA Assay Kit available from the manufacturer. Various commercial manufacturers offer quantitative PCR assays for detecting residual host cell DNA, e.g., AppTec™ Laboratory Services, BioReliance™, Althea Technologies, etc. A comparison of a chemiluminescent hybridisation assay and the total DNA Threshold™ system for measuring host cell DNA contamination of a human viral vaccine has been described.

Pharmaceutical Compositions

Compositions of the invention are pharmaceutically acceptable. Compositions of the invention include vaccines. They may include components in addition to the antigen and adjuvant, e.g., they will typically include one or more pharmaceutical carrier(s) and/or excipient(s), which are well known in the art.

The composition may include preservatives such as thiomersal or 2-phenoxyethanol. It is preferred, however, that the vaccine should be substantially free from (e.g., less than 5 μg/ml) mercurial material, e.g., thiomersal-free. Vaccines containing no mercury are more preferred, and a-tocopherol succinate can be included as an alternative to mercurial compounds. Preservative-free vaccines are most preferred.

To control tonicity, it is preferred to include a physiological salt, such as a sodium salt. Sodium chloride (NaCl) is preferred, which may be present at between 1 and 20 mg/ml. Other salts that may be present include potassium chloride, potassium dihydrogen phosphate, disodium phosphate dehydrate, magnesium chloride, calcium chloride, etc.

Compositions will generally have an osmolality of between 200 mOsm/kg and 400 mOsm/kg, preferably between 240-360 mOsm/kg, and will more preferably fall within the range of 290-310 mOsm/kg. Osmolality has previously been reported not to have an impact on pain caused by vaccination, but keeping osmolality in this range is nevertheless preferred.

Compositions may include one or more buffers. Typical buffers include: a phosphate buffer; a Tris buffer; a borate buffer; a succinate buffer; a histidine buffer (particularly with an aluminum hydroxide adjuvant); or a citrate buffer. Buffers will typically be included in the 5-20 mM range.

The pH of a composition will generally be between 5.0 and 8.1, and more typically between 6.0 and 8.0, e.g., 6.5 and 7.5, or between 7.0 and 7.8. A manufacturing process of the invention may therefore include a step of adjusting the pH of the bulk vaccine prior to packaging.

The composition is preferably sterile. The composition is preferably non-pyrogenic, e.g., containing <1 EU (endotoxin unit, a standard measure) per dose, and preferably <0.1 EU per dose. The composition is preferably gluten free.

Compositions of the invention may include detergent e.g., a polyoxyethylene sorbitan ester surfactant (known as "Tweens"), an octoxynol (such as octoxynol-9 (Triton X-100) or t-octylphenoxypolyethoxyethanol), a cetyl trimethyl ammonium bromide ("CTAB"), or sodium deoxycholate, particularly for a split or surface antigen vaccine. The detergent may be present only at trace amounts. Thus the vaccine may include less than 1 mg/ml each of octoxynol-10 and polysorbate 80. Other residual components in trace amounts could be antibiotics (e.g., neomycin, kanamycin, polymyxin B).

The composition may include material for a single immunization, or may include material for multiple immunizations, which is also referred to as a "multidose" kit. The inclusion of a preservative is preferred in multidose arrangements. As an alternative (or in addition) to including a preservative in multidose compositions, the compositions may be contained in a container having an aseptic adaptor for removal of material.

Influenza vaccines are typically administered in a dosage volume (unit dose) of about 0.5 ml, although a half dose (i.e., about 0.25 ml) may be administered to children according to the invention.

Compositions and kits are preferably stored at between 2° C. and 8° C. They should not be frozen. They should ideally be kept out of direct light.

The antigen and emulsion in a composition will typically be in admixture, although they may initially be presented in the form of a kit of separate components for extemporaneous admixing. Compositions will generally be in aqueous form when administered to a subject.

Kits of the Invention

Compositions of the invention may be prepared extemporaneously, at the time of delivery. Thus the invention provides kits including the various components ready for mixing. The kit allows the adjuvant and the antigen to be kept separately until the time of use.

The components are physically separate from each other within the kit, and this separation can be achieved in various ways. For instance, the two components may be in two separate containers, such as vials. The contents of the two vials can then be mixed e.g. by removing the contents of one vial and adding them to the other vial, or by separately removing the contents of both vials and mixing them in a third container.

In a preferred arrangement, one of the kit components is in a syringe and the other is in a container such as a vial. The syringe can be used (e.g., with a needle) to insert its contents into the second container for mixing, and the mixture can then be withdrawn into the syringe. The mixed contents of the syringe can then be administered to a patient, typically through a new sterile needle. Packing one component in a syringe eliminates the need for using a separate syringe for patient administration.

In another preferred arrangement, the two kit components are held together but separately in the same syringe, e.g., a dual-chamber syringe. When such syringe is actuated (e.g., during administration to a patient) then the contents of the two chambers are mixed. This arrangement avoids the need for a separate mixing step at the time of use.

The kit components will generally be in aqueous form. In some arrangements, a component (typically an antigen component rather than an adjuvant component) is in dry form (e.g., in a lyophilized form), with the other component being in aqueous form. The two components can be mixed in order to reactivate the dry component and give an aqueous composition for administration to a patient. A lyophilized component will typically be located within a vial rather than a syringe. Dried components may include stabilizers such as lactose, sucrose or mannitol, as well as mixtures thereof e.g. lactose/sucrose mixtures, sucrose/mannitol mixtures, etc. One possible arrangement uses an aqueous adjuvant component in a pre-filled syringe and a lyophilized antigen component in a vial.

Packaging of Compositions or Kit Components

Suitable containers for compositions of the invention (or kit components) include vials, syringes (e.g. disposable syringes), nasal sprays, etc. These containers should be sterile.

Where a composition/component is located in a container, such as a vial, such container is optionally made of a glass or plastic material. In some embodiments, such container is a siliconized container. The vial is preferably sterilized before the composition is added to it. To avoid problems with latex-sensitive patients, vials are preferably sealed with a latex-free stopper, and the absence of latex in all packaging material is preferred. The vial may include a single dose of vaccine, or it may include more than one dose (i.e., a "multidose" vial), e.g., 10 doses. In some embodiments, vials are made of colorless glass.

A vial can have a cap (e.g., a Luer lock) adapted such that a pre-filled syringe can be inserted into the cap, the contents of the syringe can be expelled into the vial (e.g., to reconstitute lyophilized material therein), and the contents of the vial can be removed back into the syringe. After removal of the syringe from the vial, a needle can then be attached and the composition can be administered to a patient. The cap is preferably located inside a seal or cover, such that the seal or cover has to be removed before the cap can be accessed. A vial may have a cap that permits aseptic removal of its contents, particularly for multidose vials.

Where a component is packaged into a syringe, the syringe may have a needle attached to it. If a needle is not attached, a separate needle may be supplied with the syringe for assembly and use. Such a needle may be sheathed. Safety needles are preferred. 1-inch 23-gauge, 1-inch 25-gauge and ⅝-inch 25-gauge needles are typical. Syringes may be provided with peel-off labels on which the lot number, influenza season and expiration date of the contents may be printed, to facilitate record keeping. The plunger in the syringe preferably has a stopper to prevent the plunger from being accidentally removed during aspiration. The syringes may have a latex rubber cap and/or plunger. Disposable syringes contain a single dose of vaccine. The syringe will generally have a tip cap to seal the tip prior to attachment of a needle, and the tip cap is preferably made of a butyl rubber. If the syringe and needle are packaged separately then the needle is preferably fitted with a butyl rubber shield. Useful syringes are those marketed under the trade name "Tip-Lok"™.

Containers may be marked to show a half-dose volume e.g. to facilitate delivery to children. For instance, a syringe containing a 0.5 ml dose may have a mark showing a 0.25 ml volume.

Where a glass container (e.g., a syringe or a vial) is used, then it is preferred to use a container made from a borosilicate glass rather than from a soda lime glass. In some embodiments, a container is a siliconized container, such as a siliconized glass container.

A kit or composition may be packaged (e.g., in the same box) with a leaflet including details of the vaccine e.g. instructions for administration, details of the antigens within the vaccine, etc. The instructions may also contain warnings e.g. to keep a solution of adrenaline readily available in case of anaphylactic reaction following vaccination, etc.

Methods of Treatment, and Administration of the Vaccine

Compositions of the invention are suitable for administration to human patients, and the invention provides a method of raising an immune response in a patient, comprising the step of administering a composition of the invention to the patient. As described above, in some embodiments, the patient is an immunocompromised individual on an immunomodulatory therapy (e.g., a statin therapy, an NSAID therapy, etc.).

These methods and uses will generally be used to generate an antibody response, preferably a protective antibody response. Methods for assessing antibody responses, neutralising capability and protection after influenza virus vaccination are well known in the art. Human studies have shown that antibody titers against hemagglutinin of human influenza virus are correlated with protection (a serum sample hemagglutination-inhibition titer of about 30-40 gives around 50% protection from infection by a homologous virus). Antibody responses are typically measured by hemagglutination inhibition (HI), by microneutralization (Micro-NT), and/or by single radial hemolysis (SRH) but any other suitable methods may be employed. Such assay techniques are well known in the art.

As used herein, the terms "administering," "administration" and the like, refer to making a pharmaceutical composition (such as vaccines) available to a subject's body, locally or systemically, by any suitable route(s). Compositions of the invention can be administered in various ways. The most preferred immunization route is by intramuscular injection (e.g., into the arm or leg), but other available routes include subcutaneous injection, intranasal, oral, mucosal, transmucosal, parenteral, intradermal, transcutaneous, transdermal, etc. A more complete list of administration routes can be found at: www.fda.gov/Drugs/DevelopmentApprovalProcess/FormsSubmissionRequirements/ElectronicSubmissions/DataStandardsManualmonographs/ucm071667.htm.

Preferred compositions of the invention will satisfy 1, 2 or 3 of the CHMP criteria for adult efficacy for each influenza strain, even though they are administered to children. These criteria are: (1) >70% seroprotection; (2) >40% seroconversion or significant increase; and/or (3) a GMT increase of >2.5-fold. In elderly (>65 years), these criteria are: (1) >60% seroprotection; (2) >30% seroconversion; and/or (3) a GMT increase of >2-fold.

The invention is particularly useful for raising immune responses that are protective against different influenza virus strains, such as A and B virus strains.

As used herein, the terms "effective amount" and "effective dose" refer to an amount or dose of a compound or composition that is sufficient to fulfill its intended purpose(s), i.e., eliciting a desired biological or medicinal response in a tissue or subject at an acceptable benefit/risk ratio. For example, in certain embodiments of the present invention, the purpose(s) may be to induce or augment a desired immune response in a subject. The relevant intended purpose may be objective (i.e., measurable by some test or marker) or subjective (i.e., subject gives an indication of or feels an effect). In some embodiments, an effective amount is an amount that, when administered to a population of subjects that meets certain criteria (for example, as determined by medical or treatment history, genetic or age profile, etc.), a statistically significant response is obtained among the population. An effective amount is commonly administered in a dosing regimen that may comprise multiple unit doses. For any particular pharmaceutical agent, an effective amount (and/or an appropriate unit dose within an effective dosing regimen) may vary, for example, depending on route of administration, population profiles, and so on. Those of ordinary skill in the art will appreciate that in some embodiments of the invention, a unit dosage may be considered to contain an effective amount if it contains an amount appropriate for administration in the context of a dosage regimen correlated with a positive outcome.

Treatment with compositions of the invention can be by a single dose schedule or a multiple dose schedule. Thus, in any particular influenza season (e.g., in a given 12 month period, typically in autumn or winter) a patient may receive a single dose of a composition of the invention or more than one dose of composition of the invention (e.g., two doses). Where treatment comprises administration of two or more doses of compositions of the invention, each dose will generally not be given at substantially the same time i.e., they will not be administered during the same visit to a vaccination center. The time between successive administration of compositions of the invention is typically at least n days, where n is selected from 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 42, 49, 56 or more. Typically, two doses are administered at least 1 week apart (e.g., about 2 weeks, about 3 weeks, about 4 weeks, about 6 weeks, about 8 weeks, about 12 weeks, about 16 weeks, etc.). Giving two doses separated by from 25-30 days (e.g., 28 days) is particularly useful. The time between doses will typically be no longer than 6 months. The doses may be given about 4 weeks apart from each other e.g., at day 0 and then at about day 28. Separation of dosing in this way has been found to give good immune responses.

Where compositions of the invention are used in a primary immunization schedule, dose(s) with compositions of the invention are followed by administration of one or more booster vaccines (e.g., 1, 2, 3, or more booster vaccines). Suitable timing between priming and administration of booster vaccine can be routinely determined. The time between administration of a priming dose and administration of a booster vaccine is typically at least p months, where p is selected from 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, or more. Ideally, p is 9 or more, and may be within the range of 9-30.

In a multiple dose schedule the various doses may be given by the same or different routes, e.g., a parenteral prime and mucosal boost, a mucosal prime and parenteral boost, etc. Typically, but not necessarily, they will be given by the same route. Vaccines produced by the invention may be administered to patients at substantially the same time as (e.g., during the same medical consultation or visit to a healthcare professional or vaccination center) other vaccines, e.g., at substantially the same time as a measles vaccine, a mumps vaccine, a rubella vaccine, a MMR vaccine, a varicella vaccine, a MMRV vaccine, a diphtheria vaccine, a tetanus vaccine, a pertussis vaccine, a DTP vaccine, a conjugated *H. influenzae* type b vaccine, an inactivated poliovirus vaccine, a hepatitis B virus vaccine, a meningococcal conjugate vaccine (such as a tetravalent A-C-W135-Y vaccine), a pneumococcal conjugate vaccine, etc.

Similarly, vaccines of the invention may be administered to patients at substantially the same time as (e.g., during the same medical consultation or visit to a healthcare professional) an antiviral compound, and in particular an antiviral compound active against influenza virus (e.g., oseltamivir and/or zanamivir). These antivirals include neuraminidase inhibitors, such as a (3R,4R,5S)-4-acetylamino-5-amino-3 (I-ethylpropoxy)-I-cyclohexene-I-carboxylic acid or 5-(acetylamino)-4-[(aminoiminomethyl)-amino]-2,6-anhydro-3,4,5-trideoxy-D-glycero-D-galactonon-2-enonic acid, including esters thereof (e.g. the ethyl esters) and salts thereof (e.g. the phosphate salts). A preferred antiviral is (3R,4R,5S)-4-acetylamino-5-amino-3(I-ethylpropoxy)-1-cyclohexene-1-carboxylic acid, ethyl ester, phosphate (1:1), also known as oseltamivir phosphate (TAMIFLU™).

High-Dose Flu Vaccines for Statin Recipients

For embodiments in which a high-dose vaccine is administered to a subject of a target population, such vaccine may be an unadjuvanted vaccine. In some embodiments, a target population of the present invention refers to human subjects on an immunomodulatory therapy (e.g., a statin therapy, an NSAID therapy, etc.), regardless of the subjects' age, while in other embodiments, a target population of the present invention refers to human subjects on an immunomodulatory therapy (e.g., a statin therapy, an NSAID therapy, etc.) who are also of a particular age group, e.g., aged 65 or older; aged between 18 and 64, etc. Such subjects may be on a statin therapy comprising a non-synthetic statin, a synthetic statin, or combination thereof. Although any of such populations will benefit from the invention described herein, it may be particularly beneficial to those who are on a synthetic statin therapy, who are on a long-term statin therapy, or both.

High-dose vaccines include monovalent and multivalent (e.g., trivalent and tetravalent) influenza vaccines and may contain a high-dose (e.g., 50 μg, 60 μg, 70 μg, 80 μg, 90 μg) each of the strains. Such vaccine compositions may be formulated as an injectable sterile suspension (e.g., 0.5 mL) containing suitable antigen(s). Virus used to produce such compositions may optionally be produced in embryonated chicken eggs, may optionally be inactivated (e.g., with formaldehyde), may optionally be split (e.g., with a nonionic detergent), and may comprise an A/(H1N1)-like strain, an A/(H3N2)-like strain, and a B strain. To give but a few examples, A/California/7/2009 (H1N1), A/Victoria/210/

2009 (H3N2), and B/Brisbane/60/2008 strains may be formulated for one season, while A/California/7/2009 (H1N1), A/Victoria/361/2011 (H3N2), and B/Texas/6/2011 (B/Wisconsin/1/2010-like virus) strains may be formulated for another season. Such vaccine compositions may optionally be provided in ready-to-use syringes (such as 0.5 mL) and may be administered intramuscularly (IM) to a patient on a statin therapy, optionally in the deltoid area.

General

Throughout the specification, including the claims, where the context permits, the term "comprising" and variants thereof, such as "comprises" or "comprising," are to be interpreted as including the stated element (e.g., integer) or elements (e.g., integers) without necessarily excluding any other elements (e.g., integers).

The term "substantially" does not exclude "completely" e.g., a composition which is "substantially free" from Y may be completely free from Y. Where necessary, the word "substantially" may be omitted from the definition of the invention.

The term "about" in relation to a numerical value n refers to a range of numerical values considered typical or acceptable, e.g., within statistical errors, deviations or variations within a particular population, from which a relevant set of data is obtained for certain measurements or analyses. Those skilled in the art can readily understand such ranges. For example, a numerical value n may mean (n ±1%), (n ±1%), (n ±2%), (n ±3%), (n ±4%), (n ±5%), (n ±6%), (n ±7%), (n ±8%), (n ±9%), (n ±10%), (n ±1%), (n ±12%), (n ±13%), (n ±14%), (n ±15%), (n ±16%), (n ±17), (n ±18%), (n ±19%), (n ±20%) and so on.

Unless specifically stated, a process comprising a step of mixing two or more components does not require any specific order of mixing. Thus components can be mixed in any order. Where there are three components then two components can be combined with each other, and then the combination may be combined with the third component, etc.

Where animal (and particularly bovine) materials are used in the culture of cells, they should be obtained from sources that are free from transmissible spongiform encaphalopathies (TSEs), and in particular free from bovine spongiform encephalopathy (BSE). Overall, it is preferred to culture cells in the total absence of animal-derived materials.

Where a compound is administered to the body as part of a composition then that compound may alternatively be replaced by a suitable pro-drug.

Where a cell substrate is used for reassortment or reverse genetics procedures, it is preferably one that has been approved for use in human vaccine production, e.g., as in European Pharmacopoeia general chapter 5.2.3., "Cell substrates for production of vaccines for human use."

Accordingly, the present invention encompasses, but is not limited to, the following embodiments:

1. A method for enhancing an immune response in a subject, the method comprising the steps of:
  selecting a subject that is immunocompromised or at risk of immunosuppression; and,
  administering to the subject a vaccine comprising an adjuvant, a high-dose antigen, or combination thereof in an amount effective to enhance an immune response to the vaccine in the subject.

2. A method for enhancing an immune response, the method comprising the steps of:
  administering to a subject a vaccine comprising an adjuvant, a high-dose antigen, or combination thereof in an amount effective to enhance an immune response to the vaccine in the subject,
  wherein the subject is immunocompromised or at risk of immunosuppression.

3. A method for administering a vaccine to a subject receiving an immunomodulatory therapy in an amount effective to elicit a protective immune response to the vaccine antigen(s).

4. A method for treating an immunocompromised subject comprising a step of administering to the subject a pharmaceutical composition in an amount effective to elicit an immune response in the subject.

5. A composition for use in a method for enhancing an immune response in a subject receiving an immunomodulatory therapy in an amount effective to enhance an immune response in the subject.

6. A vaccine composition for a patient on an immunomodulatory therapy.

7. A vaccine composition for use in a patient on an immunomodulatory therapy.

8. A vaccine composition for prevention of an infection in a patient on an immunomodulatory therapy.

9. A composition for use as a medicament for treating a subject who is immunocompromised.

10. Use of a composition for the manufacture of a medicament for raising an immune response in a subject who is immunocompromised.

11. A method for manufacturing an adjuvanted and/or high-dose vaccine, wherein the vaccine is for use in a subject who is immunocompromised.

12. The composition, method, or use of any one of the preceding embodiments, wherein the subject has a condition associated with compromised immunity.

13. The composition, method, or use of any one of the preceding embodiments, wherein the subject is on a statin therapy, an NSAID therapy, or combination thereof.

14. The composition, method, or use of any one of the preceding embodiment, wherein the subject is:
  65 years or older;
  60 years or older;
  45 years or older;
  between the age of 45 and 64;
  between the age of 18 and 64; or,
  an infant.

15. The composition, method, or use of any one of the preceding embodiment, wherein the subject has a disease or disorder associated with impaired immunity.

16. The composition, method, or use of any one of the preceding embodiment, wherein the subject is on an immunomodulatory therapy.

17. The composition, method, or use of any one of the preceding embodiment, wherein the subject has been on the therapy for at least 1 week.

18. The composition, method, or use of any one of the preceding embodiment, wherein the subject has been on the therapy for at least 2 weeks, at least 3 weeks, at least 4 weeks, or longer.

18. The composition, method, or use of any one of the preceding embodiment, wherein the subject is not currently on a therapy but was on a therapy which terminated within the last 3 months.

19. The composition, method, or use of any one of the preceding embodiment, wherein the subject is not currently on a therapy but is scheduled to be on a therapy in the next 3 months.

20. The composition, method, or use of any one of the preceding embodiment, wherein the subject is on a statin therapy, an NSAID therapy, an interferon therapy, an antipsychotic and/or antidepressant therapy, or any combinations thereof.

21. The composition, method, or use of any one of the preceding embodiment, wherein the statin therapy comprises a synthetic statin, a non-synthetic statin, or combination thereof.

22 The composition, method, or use of any one of the preceding embodiment, wherein the statin therapy comprises a statin selected from the group consisting of:

Pravastatin, Simvastatin, Lovastatin and Mevastatin, Fluvastatin, Atorvastatin, Cerivastatin, Rosuvastatin and Pitavastatin.

23. The composition, method, or use of any one of the preceding embodiment, wherein the statin therapy comprises a synthetic statin selected from the group consisting of:

Fluvastatin, Atorvastatin, Cerivastatin, Rosuvastatin and Pitavastatin.

24. The composition, method, or use of any one of the preceding embodiment, wherein the NSAID therapy comprises one or more of the following:

Salicylates (e.g., Aspirin (acetylsalicylic acid), Diflunisal (Dolobid™), Salsalate (Disalcid™) and Choline Magnesium Trisalicylate (Trilisate™)); Propionic acid derivatives (e.g., Ibuprofen, Dexibuprofen, Naproxen, Fenoprofen, Ketoprofen, Dexketoprofen, Flurbiprofen, Oxaprozin and Loxoprofen); Acetic acid derivatives (e.g., Indomethacin, Tolmetin, Sulindac, Etodolac, Ketorolac, Diclofenac, Aceclofenac and Nabumetone); Enolic acid (Oxicam) derivatives (e.g., Piroxicam, Meloxicam, Tenoxicam, Droxicam, Lornoxicam and Isoxicam); Anthranilic acid derivatives (Fenamates) (e.g., Mefenamic acid, Meclofenamic acid, Flufenamic acid and Tolfenamic acid); Selective COX-2 inhibitors (Coxibs) (e.g., Celecoxib, Rofecoxib, Valdecoxib, Parecoxib, Lumiracoxib, Etoricoxib and Firocoxib); Sulfonanilides (e.g., Nimesulide) and others, such as Licofelone, H-harpagide and Lysine clonixinate.

25. The composition, method, or use of any one of the preceding embodiment, wherein the composition comprises an adjuvant.

26. The composition, method, or use of any one of the preceding embodiment, wherein the composition comprises a surfactant.

27. The composition, method, or use of any one of the preceding embodiment, wherein the composition comprises an oil-in-water emulsion.

28. The composition, method, or use of any one of the preceding embodiment, wherein the composition comprises an aluminum salt adjuvant.

29. The composition, method, or use of any one of the preceding embodiment, wherein the composition comprises an aluminum phosphate adjuvant and/or an aluminum hydroxide adjuvant.

30. The composition, method, or use of any one of the preceding embodiment, wherein the composition comprises a TLR agonist.

31. The composition, method, or use of any one of the preceding embodiment, wherein the composition comprises virosomes.

32. The composition, method, or use of any one of the preceding embodiment, wherein the composition comprises squalene.

33. The composition, method, or use of any one of the preceding embodiment, wherein the composition comprises a polysorbate.

34. The composition, method, or use of any one of the preceding embodiment, wherein the composition comprises squalene, polysorbate 80, and sorbitan trioleate.

35. The composition, method, or use of any one of the preceding embodiment, wherein the composition comprises about 4.3% squalene, about 0.5% polysorbate 80 and about 0.48% sorbitan trioleate by weight.

36. The composition, method, or use of any one of the preceding embodiment, wherein the composition is or comprises a vaccine.

37. The composition, method, or use of any one of the preceding embodiment, wherein the composition is or comprises an antigen.

38. The composition, method, or use of any one of the preceding embodiment, wherein the composition is or comprises a high-dose antigen, a standard-dose antigen, or a low-dose antigen.

39. The composition, method, or use of any one of the preceding embodiment, wherein the composition comprises between a 1/8 and a ten-fold the amount of a standard-dose antigen.

40. The composition, method, or use of any one of the preceding embodiment, wherein the composition comprises between a two-fold and a ten-fold the amount of a standard-dose antigen.

41. The composition, method, or use of any one of the preceding embodiment, wherein the composition does not contain an adjuvant.

42. The composition, method, or use of any one of the preceding embodiment, wherein the composition does not contain an oil-in-water emulsion adjuvant.

43. The composition, method, or use of any one of the preceding embodiment, wherein the composition is an influenza vaccine.

44. The composition, method, or use of any one of the preceding embodiment, wherein the composition is a multivalent influenza vaccine.

45. The composition, method, or use of any one of the preceding embodiment, wherein the influenza vaccine comprises between about 30 µg and about 150 µg of antigen per strain.

46. The composition, method, or use of any one of the preceding embodiment, wherein the influenza vaccine comprises about 60 µg of antigen per strain.

47. The composition, method, or use of any one of the preceding embodiment, wherein the influenza vaccine comprises an H1N1 strain, an H3N2 strain, a B strain, or any combination thereof.

Exemplification

As mentioned above, statin therapy has been associated with secondary effects on the immune system. These effects include immunomodulatory and anti-inflammatory effects. Since many patients who routinely take statins are elderly and the elderly are at higher risk of the complications of influenza (Thompson, W. W., Shay, D. K., Weintraub, E., Brammer, L., Cox, N., Anderson, L. J., & Fukuda, K. (2003). Mortality associated with influenza and respiratory syncytial virus in the United States. Jama, 289(2): 179-186), we utilized data from a large comparative immunogenicity study of adjuvanted and unadjuvanted influenza vaccines in the elderly to evaluate the influence of statin therapy on the immune response to influenza vaccine.

We utilized the immunogenicity measurements available from a comparative trial of adjuvanted versus unadjuvanted influenza vaccine in patients to evaluate the influence of statin therapy on the immune response to vaccination. Overall, data on more than 5,000 trial participants were available for analysis. Comparison of HAI geometric mean titers to influenza H1N1, H3N2 and B strains in individuals on and off chronic statin therapy revealed that titers in statin recipients were 38%, 67% and 38%, respectively, lower in statin recipients than in individuals not on statins. This immunosuppressive effect of statins on vaccine immune response was particularly dramatic in individuals on synthetic statins. These effects were seen in both the adjuvanted and unadjuvanted vaccine groups. However, since titers in the adjuvanted vaccine group were higher, the impact of statin therapy on vaccine response was at least partially counteracted by the use of adjuvanted vaccine. These results have implications both for future clinical trial design as well as for vaccine usage recommendations in the elderly.

Methods

During the influenza seasons of 2009-2010 and 2010-2011, a randomized, controlled, observer-blind clinical trial was conducted comparing the safety and immunogenicity of MF-59 adjuvanted trivalent influenza vaccine ("aTIV") and unadjuvanted TIV in over 14,000 adults older than 65 years of age in Colombia, Panama, the Philippines and the USA (Frey SE, Aplasca-De Los Reyes MR, Reynales H, Bermal NN, Nicolay U, Narasimhan V, Forleo-Neto E, and Arora AK. Comparison of the Safety and Immunogenicity of an MF-59 adjuvanted with a Non-adjuvanted seasonal influenza vaccine in Elderly Subjects. Vaccine in press). As part of this evaluation, information on statin use was collected and this was considered as a potential confounder in comparative analyses.

Blood samples were obtained on the day of vaccination and 28 days following receipt of seasonally appropriate influenza vaccine. HAI titers were determined using standard methodology (Murphy, B. R., Phelan, M. A., Nelson, D. L., Yarchoan, R., Tierney, E. L., Alling, D. W., & Chanock, R. M. (1981). Hemagglutinin-specific enzyme-linked immunosorbent assay for antibodies to influenza A and B viruses. Journal of clinical microbiology, 13(3): 554-560).

For the purposes of our current post-hoc analysis, patients were classified as being on statin therapy if they had been taking medication for 28 days or more prior to receipt of vaccination and through day 22 after vaccination. Individuals who had not received statins during this time window were considered to be controls. The small number of individuals that did not fit into either group were dropped from the analysis. Patients were further stratified as to whether they were on synthetic or natural occurring statins.

Geometric Mean Titers (GMT) and GMT ratios were then compared between the statin and control groups against the vaccine homologous influenza A strains H1N1 (California), H3N2 (Perth), and influenza B (Brisbane). In adjusted comparisons, an ANCOVA analysis included the following variables: vaccine group (aTIV, TIV), statin user in days −28 to day 22 (yes/no), high risk status (yes/no), sex, log-pre-vaccination titer and age (both continuous variables). Because an evaluation of the interaction between vaccine type and statins did not reveal an impact of the type of vaccine on the impact of statins on the immune response (p>0.05), ratios of the GMTs in statin recipients and controls were calculated for the combined study group.

Results

A total of 6961 subjects, 3479 in the MF-59 adjuvanted TIV group ("aTIV") and 3482 in the unadjuvanted TIV group ("TIV"), had day 22 HAI titers available for analysis. Overall, 2798 and 2786 aTIV and TIV recipients respectively were controls and 681 and 696 individuals respectively were determined to meet the definition of being statin users. Of the statin users, 76% of aTIV and 74% of TIV statin users were taking fermentation derived statins (Pravastatin, Simvastatin, Lovastatin, Adivocor) and the remainder were taking synthetic statins (Fluvastatin, Atorvastatin, Rosuvastatin). Overall, 75% of statin users were considered to have a high risk medical condition. The most common category was underlying neurologic disease followed by COPD, asthma, congestive heart failure, renal insufficiency and hepatic disease. (Table 1). Overall, 55% of statin users and 68% of controls were male and 74% of controls and 67% of statin users were between 65-75 years of age with the remainder being older than 75 years of age. The results of HAI GMTs against the three influenza vaccine strains are shown in Tables Two with the day one ratio being adjusted for age, risk group and vaccine and the day 22 ratio also adjusted for pre-titer.

TABLE 1

Co-morbidities in each group

| | No Statins | | On Statins day −22 to day 28 | |
| Co-morbidity | aTIV (N = 2798) | TIV (N = 2786) | aTIV (N = 681) | TIV (N = 696) |
|---|---|---|---|---|
| Asthma | 120 (4%) | 112 (4%) | 42 (6%) | 43 (6%) |
| CHF | 46 (2%) | 46 (2%) | 31 (5%) | 33 (5%) |
| COPD | 105 (4%) | 113 (4%) | 66 (10%) | 61 (9%) |
| Hepatic disease | 9 (<1%) | 9 (<1%) | 4 (<1%) | 4 (<1%) |
| Neurological... | 591 (21%) | 576 (21%) | 485 (71%) | 469 (67%) |
| Renal insufficiency | 28 (1 %) | 27 (<1%) | 21 (3%) | 30 (4%) |

TABLE 2

GMT Titer by Statin Use and Vaccine Group for each of three influenza strains

| Influenza Strain | Day | | No Statin Group | | Statin Group | |
| | | | aTIV | TIV | aTIV | TIV |
|---|---|---|---|---|---|---|
| H1N1 California 09 | 1 | n | 2797 | 2784 | 681 | 696 |
| | | GMT | 12 | 12 | 22 | 24 |
| | | 95% CI | 12-13 | 11-12 | 19-24 | 21-26 |
| | | Ratio ST−/ ST+ (95% CI) | | 0.62 (0.57-0.67) | | |
| | 22 | n | 2797 | 2786 | 681 | 696 |
| | | GMT | 196 | 140 | 170 | 129 |
| | | 95% CI | 185-206 | 133-148 | 155-188 | 117-142 |
| | | Ratio ST−/ ST+ (95% CI) | | 1.38 (1.27-1.50) | | |
| H3N2 Perth 09 | 1 | n | 2797 | 2784 | 681 | 696 |
| | | GMT | 50 | 49 | 47 | 44 |
| | | 95% CI | 47-53 | 46-52 | 42-52 | 40-49 |
| | | Ratio ST−/ ST+ (95% CI) | | 1.13 (1.02-1.25) | | |

TABLE 2-continued

GMT Titer by Statin Use and Vaccine Group
for each of three influenza strains

| Influenza | | | No Statin Group | | Statin Group | |
|---|---|---|---|---|---|---|
| Strain | Day | | aTIV | TIV | aTIV | TIV |
| | 22 | n | 2797 | 2785 | 681 | 696 |
| | | GMT | 669 | 421 | 356 | 209 |
| | | 95% CI | 638-701 | 402-441 | 324-392 | 190-230 |
| | | Ratio ST-/ ST+ (95% CI) | | 1.67 (1.54-1.80) | | |
| B Brisbane 08 | 1 | n | 2798 | 2786 | 681 | 696 |
| | | GMT | 9.6 | 9.4 | 16 | 17 |
| | | 95% CI | 9.2-9.9 | 9.1-9.8 | 15-18 | 15-18 |
| | | Ratio ST-/ ST+ (95% CI) | | 0.68 (0.64-0.72) | | |
| | 22 | n | 2798 | 2786 | 681 | 696 |
| | | GMT | 50 | 43 | 48 | 40 |
| | | 95% CI | 47-52 | 41-46 | 44-52 | 37-44 |
| | | Ratio ST-/ ST+ (95% CI) | | 1.38 (1.28-1.49) | | |

As can be seen in Table Two, overall pre-titers were equal in each vaccine group for each of the three strains. However, individuals on statins had higher pre-titers against H1N1 and influenza B whereas the reverse was true for influenza H3N2. Post vaccination day 22 titers were significantly higher in aTIV recipients for all three antigens. In analyses comparing statin recipients with controls regardless of vaccine type, the GMT titer ratio was 38% higher in controls for H1N1, 67% higher for H3N2 and 38% higher for influenza B indicating a marked reduction in immunogenicity in statin recipients for all three antigens despite adjustment for age, high risk group status, pre-titer and type of vaccine received. Similar data was obtained when testing against heterologous strains of influenza B (Malaysia), and H3N2 (Brisbane and Wisconsin) (data not shown).

Results stratified by statin type are shown in Table 3.

TABLE 3

Influence of Statin Type on Vaccine
Response as assessed at day 22

| Homologous Strain | Ratio ST-/ Fermentation ST+ (95% CI) | Ratio ST-/ Synthetic ST+ (95% CI) | Ratio Fermentation/ Synthetic (95% CI) |
|---|---|---|---|
| B Brisbane 08 | 1.32 (1.21-1.43) | 1.59 (1.39-1.81) | 1.21 (1.05-1.39) |
| H1N1 California 09 | 1.31 (1.20-1.44) | 1.62 (1.40-1.87) | 1.23 (1.05-1.44) |
| H3N2 Perth 09 | 1.59 (1.46-1.73) | 1.91 (1.68-2.19) | 1.20 (1.04-1.39) |

Patients receiving fermentation derived statins had higher titers than those on synthetic statins indicating that the latter had a greater immunosuppressive effect on influenza vaccine response. Similar non-statically significant trends were also seen in testing against heterologous strains.

Discussion

Within developing countries, life expectancy has been steadily increasing with an increasing proportion of the populations in developing countries being elderly (Mathers, C. D., Sadana, R., Salomon, J. A., Murray, C. J., & Lopez, A. D. (2001). Healthy life expectancy in 191 countries, 1999. The Lancet, 357(9269): 1685-1691). Such improvements have been attributed to public health measures including vaccinations and medications such as statins (www.who.int/bulletin/volumes/86/2/07-040089/en/ accessed Jul. 16, 2014). Statins are widely used in adults and the elderly for treatment of hypercholesterolemia. We have shown that this class of drugs, especially synthetically derived statins, dramatically suppress the immune response to both adjuvanted and unadjuvanted influenza vaccines in the population evaluated. Surprisingly, for two of the three strains, adjuvanted vaccine was able to at least counteract this immunosuppressive effect. For the H3N2 strain tested, while adjuvanted vaccine titers were higher than those for TIV, titers in statin recipients were lower following aTIV than in controls receiving unadjuvanted vaccine.

Given the increasingly complex nature of health interventions in high-risk populations, including the elderly and those on certain medications, long-term therapy in particular, it will be important to assess potential interactions between such interventions.

Our results stand in direct contrast to studies of the impact of statins on vaccine immune response to hepatitis A vaccine and tetanus toxoid in young adults. In a study by Seigrist et al., the mean age of subjects was 24 years. In this study healthy subjects were randomized to receive atorvastin or placebo. Response to hepatitis A vaccine was assessed 28 days following receipt of vaccine. No difference in the immune response was seen between the two groups. It is important to note, however, that in contrast to our study in which statin recipients were on chronic therapy at the time of vaccination, in this hepatitis A study, study participants did not begin statin therapy until the day of vaccination (Packard R S, Schlegel S, Senouf D, Burger F, Sigaud P, Perneger T, Seigrist C A, and Mach F. Atorvastin Treatment and Vaccination Efficacy. J Clin Pharmacology 2007, 47:1022-1027). In another study, Brantly et al evaluated response to tetanus toxoid in healthy volunteers. Similar to the hepatitis A study, healthy study participants were randomized to receive atorvastin or placebo and began medication on the day of vaccination. Surprisingly, study participants in this study assigned to the statin group had three fold higher anti-TT IgG levels (Lee P Y, Sumpia P O, Byars J A, Kelly K M, Zhuang H, Shuster J S, Theriaque D W, Segal M S, Reeves W H, and Brantly M L. Short-term atorvastin treatment enhances specific antibody production following tetanus toxoid vaccination in healthy volunteers. Vaccine 2006, 24:4035-4040). The two clear differences between these studies and the results we report here are the much older age of our study group and the fact that in the tetanus toxoid and hepatitis A studies, participants had not been chronically exposed to statins at the time of vaccination. It is of course possible that one or both of these factors contribute to the contrasting study results. However, since most statin users take the medication long term, the results of these two studies have limited utility to evaluating the influence of routine statin therapy.

Studies of influenza vaccine effectiveness in the elderly have revealed suboptimal levels of effectiveness. In a study by Monto in elderly nursing home patients, vaccination was 33% against influenza like illness and 43% against pneumonia (Monto, A. S., Hornbuckle, K., & Ohmit, S. E. (2001). Influenza vaccine effectiveness among elderly nursing home residents: a cohort study. American journal of epidemiology, 154(2), 155-160). In an earlier meta-analysis study using data from twenty observational studies largely conducted between 1970s and 1980s, Gross found higher pooled estimates of vaccine efficacy of 56% (95% CI, 39% to 68%) for prevention respiratory illness, 53% (CI, 35% to 66%) for prevention of pneumonia, 50% (CI, 28% to 65%) for prevention of hospitalization, and 68% (CI, 56% to 76%) for preventing death (Gross, P. A., Hermogenes, A. W., Sacks, H. S., Lau, J., & Levandowski, R. A. (1995). The efficacy of influenza vaccine in elderly persons A meta-analysis and review of the literature. Annals of Internal medicine, 123(7), 518-527). Of interest is that estimates of efficacy against respiratory illness and pneumonia in the earlier years when statin use was less common are higher than those in the more recent study. In light of analyses disclosed here, it is also possible that these differences are due to different influenza strains and other population factors.

Statins have been considered as adjunct agents in the prevention pneumonia because their immunosuppressive effect might lower baseline inflammatory status and thus the severity of pneumonia. Observational studies of statin use in COPD have reported reductions in mortality of 30%- 50% following pneumonia or infective exacerbations in statin users (Young R, Hopkins R J. Statin Use in Pneumonia. The American Journal of Medicine, Volume 126, Issue 7, e11-e12). Other studies have not found an impact of statins on pneumonia and sepsis risk (Yende S, Milbrandt E B, Kellum J A, Kong L, Delude R L, Weissfeld L A and Angus D C. Understanding the potential role of statins in pneumonia and sepsis. Critical Care Medicine 2011, 39(8): 1871-1878). Fedson has recommended consideration of statins as therapeutic agents in the treatment of pneumonia in the elderly (Fedson, D. S. (2013). Treating influenza with statins and other immunomodulatory agents. Antiviral research, 99(3), 417-435). In a commentary he states that while system biologists have suggested the use of immunomodulatory agents such as statins in the treatment of influenza, random-ized clinical trials of this approach should precede their routine use of this. Fedson similarly points out that espe-cially in pandemics where severe disease may proceed vaccine availability by many months, consideration should be given to evaluating statins as potential agents to reduce inflammation and hence severity of disease (Fedson, D. S. (2013). How will physicians respond to the next influenza pandemic?. Clinical infectious diseases, cit695).

Clearly the impact of statins on the immune system and consequent vaccine response as well as disease risk are complex. While the immunosuppressive effects of statins may be desirable in the acute disease state, the same effect can be deleterious when it impacts vaccine response. We have shown a dramatic effect of long term statin use on the immune response to influenza vaccine in the tested popula-tion. This negative effect should be taken into account when evaluating the immunogenicity and effectiveness of influ-enza vaccines affected population and potentially in consid-ering preferential use of adjuvanted vaccines and/or high-dose vaccines such populations of subjects to counteract drug-induced immunosuppression.

The various features and embodiments of the present invention, referred to in individual sections above apply, as appropriate, to other sections, mutatis mutandis. Conse-quently features specified in one section may be combined with features specified in other sections, as appropriate.

Those skilled in the art will recognize, or be able to ascertain using no more than routine experimentation, many equivalents to the specific embodiments of the invention described herein. Such equivalents are intended to be encompassed by the following claims.

The invention claimed is:

1. A method of vaccinating an immunocompromised subject comprising administering a vaccine, wherein the vaccine is a multivalent vaccine comprising about 45 µg to about 150 µg of at least one influenza virus antigen per strain and the subject is immunocompromised and above the age of 65.

2. The method according to claim 1, wherein the multi-valent vaccine is a trivalent vaccine.

3. The method according to claim 2, wherein the vaccine is an influenza vaccine.

4. The method according to claim 3, wherein the vaccine comprises about 60 µg to about 150 µg of the at least one influenza virus antigen per strain.

5. The method according to claim 3, wherein the vaccine comprises about 60 µg of the at least one influenza virus antigen per strain.

6. The method according to claim 3, wherein the vaccine comprises an H1N1 strain, an H3N2 strain, a B strain, or any combination thereof.

7. The method according to claim 1, wherein the multi-valent vaccine is a tetravalent vaccine.

8. The method according to claim 7, wherein the vaccine is an influenza vaccine.

9. The method according to claim 8, wherein the vaccine comprises about 60 µg to about 150 µg of the at least one influenza virus antigen per strain.

10. The method according to claim 8, wherein the vaccine comprises about 60 µg of the at least one influenza virus antigen per strain.

11. The method according to claim 8, wherein the vaccine comprises an H1N1 strain, an H3N2 strain, a B strain, or any combination thereof.

12. The method according to claim 1, wherein the subject is immunocompromised following administration of at least one statin, at least one NSAID, at least one chemotherapeu-tic, or at least one immunosuppressing agent.

13. The method according to claim 1, wherein the subject is immunocompromised following administration of at least one immunosuppressing agent administered following organ transplant.

14. A method of vaccinating a subject comprising admin-istering a vaccine, wherein the vaccine is a tetravalent vaccine comprising about 45 µg to about 150 µg of at least one high-dose influenza virus antigen and the subject is immunocompromised and above the age of 65.

15. The method according to claim 14, wherein the vaccine is an influenza vaccine.

16. The method according to claim 15, wherein the vaccine comprises about 60 µg to about 150 µg of the at least one influenza virus antigen per strain.

17. The method according to claim 15, wherein the vaccine comprises about 60 µg of the at least one influenza virus antigen per strain.

18. The method according to claim 15, wherein the vaccine comprises an H1N1 strain, an H3N2 strain, a B strain, or any combination thereof.

19. The method according to claim 14, wherein the subject is immunocompromised following administration of at least one statin, at least one NSAID, at least one chemo-therapeutic, or at least one immunosuppressing agent.

20. The method according to claim 14, wherein the subject is immunocompromised following administration of at least one immunosuppressing agent administered follow-ing organ transplant.

* * * * *